(12) United States Patent
Börtlein et al.

(10) Patent No.: US 10,064,719 B2
(45) Date of Patent: Sep. 4, 2018

(54) TRANSCATHETER VALVE PROSTHESIS

(71) Applicant: HIGHLIFE SAS, Paris (FR)

(72) Inventors: Georg Börtlein, Paris (FR); Malek Nasr, Paris (FR)

(73) Assignee: HIGHLIFE SAS, Paris (FR)

( * ) Notice: Subject to any disclaimer, the term of this patent is extended or adjusted under 35 U.S.C. 154(b) by 33 days.

(21) Appl. No.: 14/204,662

(22) Filed: Mar. 11, 2014

(65) Prior Publication Data

US 2015/0257882 A1 Sep. 17, 2015

(51) Int. Cl.
*A61F 2/24* (2006.01)
*A61F 2/848* (2013.01)

(52) U.S. Cl.
CPC .......... *A61F 2/2418* (2013.01); *A61F 2/2409* (2013.01); *A61F 2002/8483* (2013.01); *A61F 2220/0008* (2013.01); *A61F 2220/0016* (2013.01); *A61F 2230/008* (2013.01); *A61F 2230/0054* (2013.01); *A61F 2230/0067* (2013.01); *A61F 2230/0078* (2013.01); *A61F 2250/006* (2013.01)

(58) Field of Classification Search
CPC ........ A61F 2/24; A61F 2/2403; A61F 2/2406; A61F 2/2409; A61F 2/2412; A61F 2/2418; A61F 2/2427; A61F 2/243; A61F 2/848; A61F 2002/8483; A61F 2002/8486
See application file for complete search history.

(56) References Cited

U.S. PATENT DOCUMENTS

| | | | | |
|---|---|---|---|---|
| 6,120,534 A | * | 9/2000 | Ruiz | A61B 17/12109 606/194 |
| 7,806,927 B2 | * | 10/2010 | Styrc | A61F 2/2409 623/2.11 |
| 8,236,049 B2 | | 8/2012 | Rowe et al. | |
| 8,323,335 B2 | | 12/2012 | Rowe et al. | |
| 8,449,605 B2 | | 5/2013 | Lichtenstein et al. | |
| 8,597,348 B2 | | 12/2013 | Rowe et al. | |
| 8,623,079 B2 | | 1/2014 | Savage et al. | |
| 8,956,404 B2 | * | 2/2015 | Bortlein | A61F 2/2418 623/2.11 |
| 9,375,312 B2 | | 6/2016 | Weber | |
| 2002/0055774 A1 | * | 5/2002 | Liddicoat | A61F 2/2409 623/2.4 |
| 2002/0099438 A1 | | 7/2002 | Furst | |

(Continued)

FOREIGN PATENT DOCUMENTS

| | | |
|---|---|---|
| DE | 697 30 840 T2 | 9/2005 |
| DE | 102005052628 A1 | 5/2007 |

(Continued)

OTHER PUBLICATIONS

Aug. 11, 2014 Office Action issued in U.S. Appl. No. 14/204,518.
(Continued)

*Primary Examiner* — David C Eastwood
(74) *Attorney, Agent, or Firm* — Oliff PLC

(57) ABSTRACT

A system for implanting a heart valve includes a radially self-expandable tubular body having an inflow end and an outflow end and a projection extending from a side surface of the tubular body toward the inflow end. The system further includes a valve disposed within and attached to the tubular body, and may include fabric that forms a pouch between the tubular body and the projection.

15 Claims, 36 Drawing Sheets

(56) References Cited

U.S. PATENT DOCUMENTS

| | | | |
|---|---|---|---|
| 2002/0193871 A1* | 12/2002 | Beyersdorf | A61F 2/2418 623/1.26 |
| 2003/0070683 A1* | 4/2003 | Deem | A61B 17/12104 128/207.16 |
| 2004/0015232 A1* | 1/2004 | Shu | A61F 2/2409 623/2.4 |
| 2004/0044406 A1* | 3/2004 | Woolfson | A61F 2/2427 623/2.11 |
| 2004/0186565 A1* | 9/2004 | Schreck | A61F 2/2418 623/2.18 |
| 2004/0243227 A1* | 12/2004 | Starksen | A61B 17/064 623/2.11 |
| 2005/0055082 A1* | 3/2005 | Ben Muvhar | A61F 2/91 623/1.15 |
| 2005/0137686 A1 | 6/2005 | Salahieh et al. | |
| 2005/0182486 A1* | 8/2005 | Gabbay | A61F 2/2409 623/2.11 |
| 2006/0058872 A1 | 3/2006 | Salahieh et al. | |
| 2007/0129795 A1* | 6/2007 | Hill | A61B 17/0469 623/2.11 |
| 2007/0142906 A1 | 6/2007 | Figulla et al. | |
| 2007/0142907 A1 | 6/2007 | Moaddeb et al. | |
| 2007/0213813 A1* | 9/2007 | Von Segesser | A61F 2/2418 623/2.18 |
| 2008/0071361 A1 | 3/2008 | Tuval et al. | |
| 2008/0071369 A1* | 3/2008 | Tuval | A61F 2/2418 623/2.38 |
| 2008/0077234 A1* | 3/2008 | Styrc | A61F 2/2409 623/2.11 |
| 2008/0077236 A1* | 3/2008 | Letac | A61F 2/2412 623/2.18 |
| 2009/0319037 A1 | 12/2009 | Rowe et al. | |
| 2010/0094411 A1* | 4/2010 | Tuval | A61F 2/2418 623/2.1 |
| 2010/0145438 A1* | 6/2010 | Barone | A61F 2/2418 623/2.1 |
| 2010/0256751 A1 | 10/2010 | Rowe et al. | |
| 2010/0312333 A1* | 12/2010 | Navia | A61F 2/2418 623/2.36 |
| 2011/0137397 A1* | 6/2011 | Chau | A61F 2/2418 623/1.11 |
| 2011/0218620 A1 | 9/2011 | Meiri et al. | |
| 2011/0238168 A1* | 9/2011 | Pellegrini | A61F 2/2412 623/2.17 |
| 2011/0264196 A1* | 10/2011 | Savage | A61F 2/2418 623/1.26 |
| 2012/0022640 A1* | 1/2012 | Gross | A61B 17/068 623/2.11 |
| 2012/0035722 A1* | 2/2012 | Tuval | A61F 2/2418 623/2.37 |
| 2012/0053682 A1* | 3/2012 | Kovalsky | A61F 2/2418 623/2.11 |
| 2012/0078353 A1* | 3/2012 | Quadri | A61F 2/2418 623/2.11 |
| 2012/0215303 A1* | 8/2012 | Quadri | A61F 2/2418 623/2.18 |
| 2013/0090726 A1 | 4/2013 | Rowe et al. | |
| 2013/0116779 A1 | 5/2013 | Weber | |
| 2013/0211508 A1* | 8/2013 | Lane | A61F 2/2403 623/2.11 |
| 2013/0226289 A1* | 8/2013 | Shaolian | A61F 2/2466 623/2.11 |
| 2013/0253642 A1* | 9/2013 | Brecker | A61F 2/2418 623/2.17 |
| 2013/0261741 A1* | 10/2013 | Accola | A61B 17/1204 623/2.11 |
| 2013/0274873 A1 | 10/2013 | Delaloye et al. | |
| 2013/0289718 A1* | 10/2013 | Tsukashima | A61F 2/2448 623/2.11 |
| 2013/0310928 A1* | 11/2013 | Morriss | A61F 2/2418 623/2.12 |
| 2014/0018915 A1* | 1/2014 | Biadillah | A61F 2/2418 623/2.17 |
| 2014/0052237 A1* | 2/2014 | Lane | A61F 2/2412 623/2.11 |
| 2014/0243966 A1* | 8/2014 | Garde | A61F 2/2409 623/2.18 |
| 2014/0277390 A1* | 9/2014 | Ratz | A61F 2/2418 623/1.26 |
| 2014/0277411 A1 | 9/2014 | Bortlein et al. | |
| 2014/0277412 A1 | 9/2014 | Bortlein et al. | |
| 2014/0277424 A1* | 9/2014 | Oslund | A61F 2/2418 623/2.38 |
| 2014/0277427 A1* | 9/2014 | Ratz | A61F 2/2409 623/2.38 |
| 2014/0324164 A1* | 10/2014 | Gross | A61F 2/2442 623/2.37 |
| 2015/0127093 A1* | 5/2015 | Hosmer | A61F 2/2418 623/2.11 |
| 2015/0142100 A1* | 5/2015 | Morriss | A61F 2/2418 623/2.4 |
| 2016/0120642 A1* | 5/2016 | Shaolian | A61F 2/2448 623/1.18 |

FOREIGN PATENT DOCUMENTS

| | | |
|---|---|---|
| DE | 10 2011 054 172 A1 | 3/2013 |
| WO | WO 2009/155561 A2 | 12/2009 |
| WO | 2010/008548 A2 | 1/2010 |
| WO | 2013/037519 A1 | 3/2013 |
| WO | WO 2013/120181 A1 | 8/2013 |

OTHER PUBLICATIONS

Liang Ma et al.; Double-crowned valved stents for off-pump mitral valve replacement; Cardiothoracic Department. The 1st Affiliated Hospital of Medical College, Zhejiang University, Hangzhou, China, Department of Cardiovascular Surgery, Centre Hospitalier Universitaire Vaudois (CHUV), Lausanne, Switzerland, European Journal of Cardio-thracic Surgery (2005), Seiten 194-199.
Oct. 23, 2015 Office Action issued in U.S. Appl. No. 14/204,171.
Nov. 30, 2015 Office Action issued in U.S. Appl. No. 14/204,517.
Jan. 20, 2016 Office Action issued in U.S. Appl. No. 14/204,629.
Feb. 3, 2016 Office Action issued in U.S. Appl. No. 14/204,394.
Jul. 28, 2016 Office Action issued in U.S. Appl. No. 14/342,237.
Mar. 11, 2016 Office Action issued in U.S. Appl. No. 14/342,237.
Jul. 13, 2016 Office Action issued in U.S. Appl. No. 14/204,394.
Jul. 13, 2016 Office Action issued in U.S. Appl. No. 14/204,629.
Sep. 13, 2016 Office Action issued in U.S. Appl. No. 14/204,327, filed Mar. 11, 2014.
Nov. 28, 2016 Office Action issued in U.S. Appl. No. 14/204,394.
Dec. 13, 2016 Office Action issued in U.S. Appl. No. 14/204,629.
May 9, 2017 Office Action issued in U.S. Appl. No. 14/204,394.
Nov. 30, 2017 Office Action issued in U.S. Appl. No. 14/204,293.

* cited by examiner

A-A

B-B

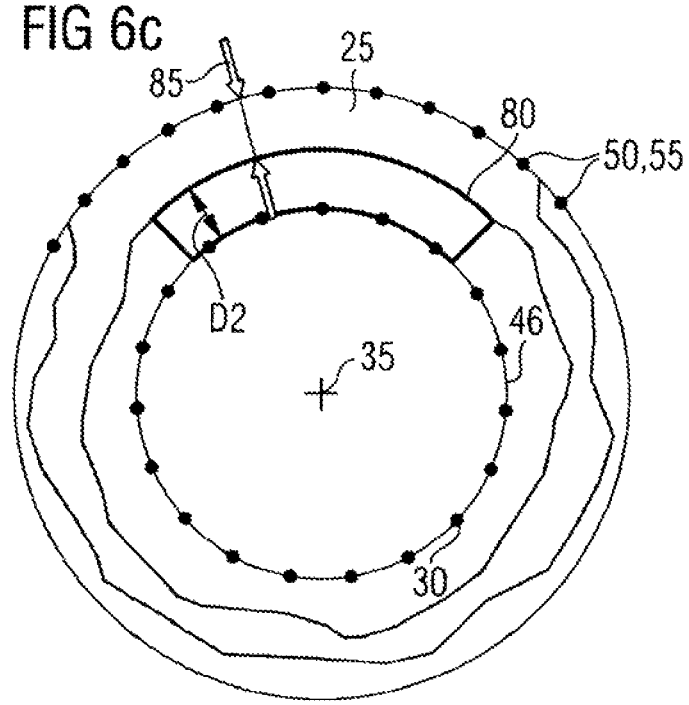
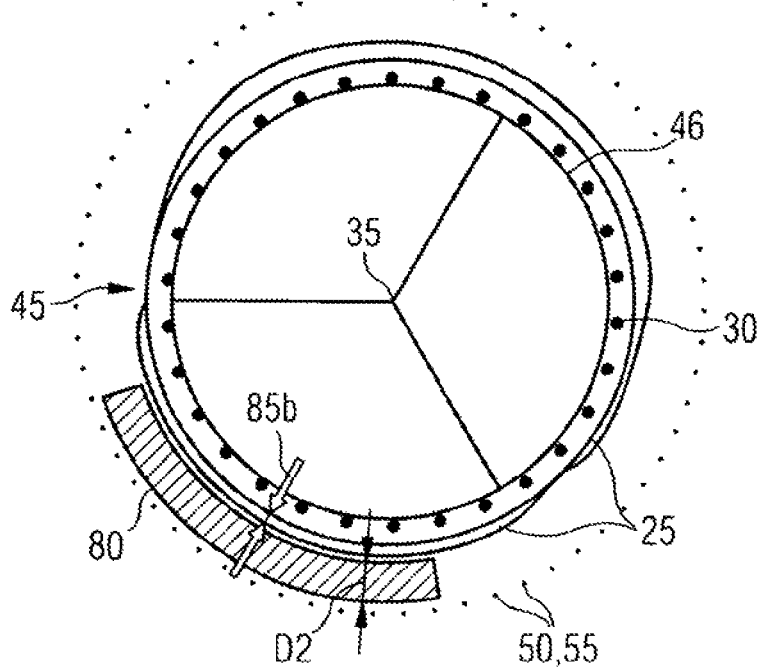

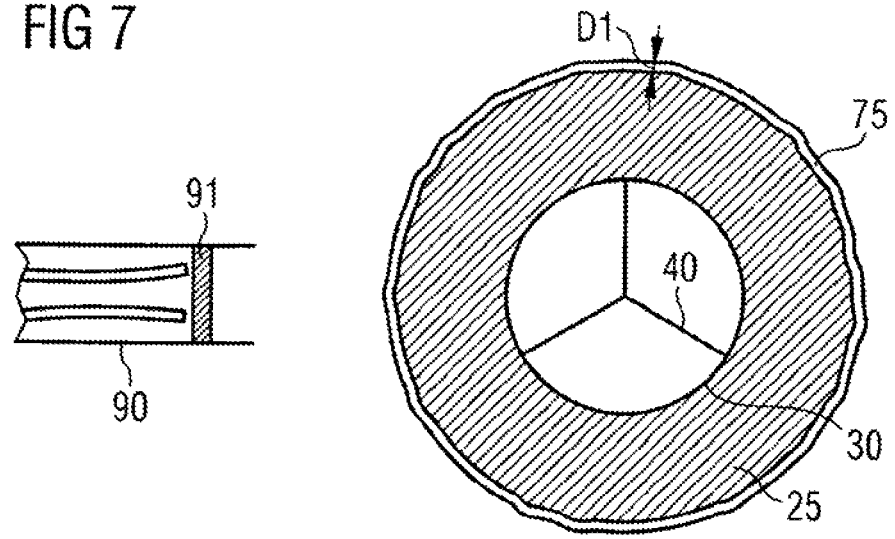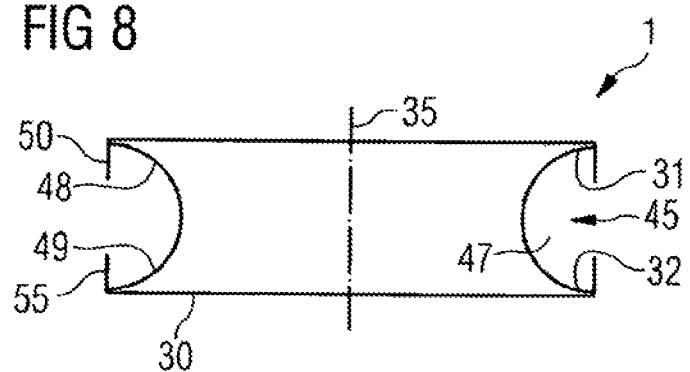

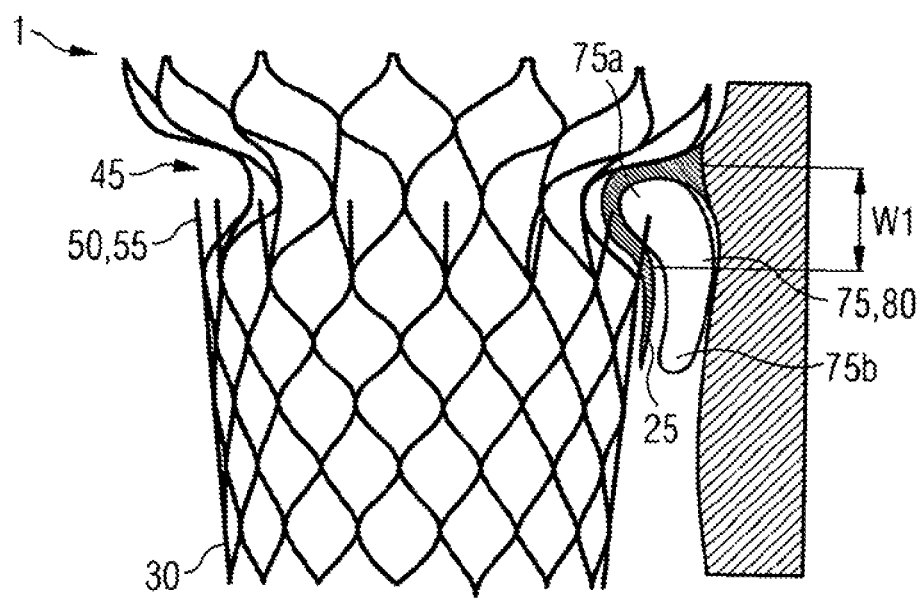

TRANSCATHETER VALVE PROSTHESIS

TECHNICAL FIELD

Embodiments generally relate to a transcatheter valve prosthesis, especially a transcatheter atrio-ventricular valve prosthesis.

BACKGROUND

Heart valve diseases are affecting approximately 300,000 people worldwide each year. Those diseases translate in abnormal leaflet tissue (excess tissue growth, tissue degradation/rupture, tissue hardening/calcifying), or abnormal tissue position through the cardiac cycle (e.g., annular dilation, ventricular reshaping) leading to a degrading valve function like leakage/blood backflow (valve insufficiency) or a resistance to blood forward flow (valve stenosis).

Accordingly, a transcatheter valve prosthesis for functional replacement of a heart valve is desirable.

SUMMARY

Various embodiments of the invention provide a system for implanting a heart valve. The system may include a radially self-expandable tubular body having an inflow end and a preformed groove disposed at an outer surface of the tubular body between the inflow end and the outflow end, wherein the preformed groove extends at least partially around the tubular body and having a circumferential opening facing radially outward of the tubular body. A valve may be disposed within and attached to the tubular body. Additionally, a trapping member may be configured to form at least a partial loop encircling the preformed groove so as to trap portions of native valve leaflets and/or chords in the preformed groove, the trapping member including one or more barbs.

Various embodiments of the invention further provide a method for implanting a replacement valve in a patient's heart. The method may include at least partially deploying from a delivery catheter a radially self-expandable tubular body having an inflow end and an outflow end, a valve disposed within a lumen of the tubular body, and a preformed groove disposed at an outer surface of the tubular body between the inflow end and the outflow end, the preformed groove having a circumferential opening facing radially outward of the tubular body. Additionally, the method may include advancing a trapping member to form at least a partial loop encircling the preformed groove and trapping portions of native valve leaflets and/or chords in the preformed groove, and at least partially piercing the portions of native valve leaflets and/or chords with one or more barbs on the trapping member to secure the tubular body to the portions of native valve leaflets and/or chords.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which:

FIG. 6c shows a schematic cross section of a transcatheter valve prosthesis along C-C in FIG. 4 including a clamping member, FIG. 6d shows a schematic cross section of a transcatheter valve prosthesis along C-C in FIG. 4 including a clamping member in another arrangement than shown in FIG. 6c.

FIG. 7 schematically shows the interaction of a transcatheter valve prosthesis, heart tissue and an elongate outer member according to embodiments, FIG. 8 shows a transcatheter valve prosthesis according to embodiments.

DESCRIPTION

Figure 1:
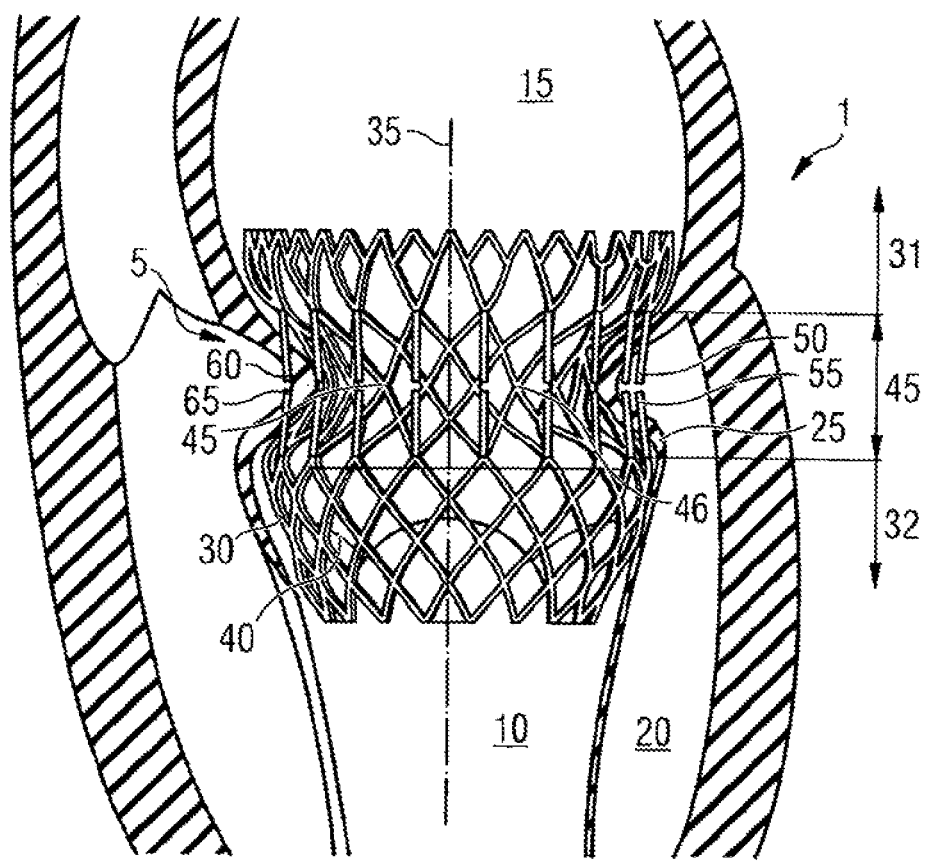
FIG. 1 shows schematically a transcatheter valve prosthesis according to embodiments, located in a connection channel of a human heart.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural and logical changes may be made without departing from the scope of the invention. The various embodiments are not necessarily mutually exclusive, as some embodiments can be combined with one or more other embodiments to form additional embodiments.

With reference to FIGS. 1, 1a, 1b and 2, a transcatheter atrioventricular valve prosthesis 1 for functional replacement of a (native) atrio-ventricular heart valve 5 in a connection channel 10 that connects an atrial heart chamber 15 with a ventricular chamber 20 and comprising a connection channel wall structure 25 may comprise a tubular body 30. The tubular body 30 may be disposed in the interior of the connection channel 10 and extend along an axis 35. The axis 35 may be the longitudinal axis 35 of the tubular body 30, which may be an elongated body. In the implanted condition, the axis 35 of the tubular body 30 may, but need not necessarily, be aligned substantially coaxial to an axis of the connection channel 10. The tubular body 30 may be radially compressible so as to facilitate approach to and insertion into the connection channel 10, e.g., using a catheter or the like, and then be radially expandable so as to closely engage the interior or inner side of the connection channel wall structure 25, and may comprise an artificial heart valve 40 (e.g., schematically shown in FIG. 6a) arranged within the tubular body 30.

The native atrio-ventricular heart valve 5 (e.g., a mitral valve or a triscupid valve) to be replaced has the generally circumferential wall structure 25 forming the connection channel 10 (or through opening) between the atrial 15 and ventricular 20 chambers of the heart. It includes a circumferential valve annulus, valve leaflets opening the connection channel/through opening and closing the connection channel through opening at a position close to the valve annulus, a generally circumferential chord structure (chordae tendinae) connected between the valve leaflets and generally circumferential papillary muscle(s), and said circumferential papillary muscle(s).

Figure 6A:
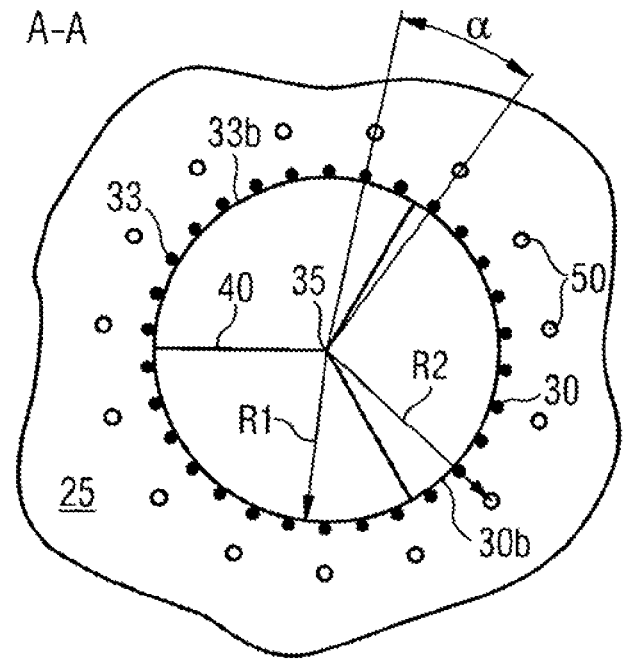
FIG. 6a shows a schematic cross section of a transcatheter valve prosthesis along A-A in FIG. 3.

The artificial heart valve 40 may be attached to the tubular body 30 and may be designed to serve as an artificial replacement valve for an atrio-venticular heart valve (for example a mitral and/or a tricuspid valve). The artificial valve 40 may comprise artificial flaps (e.g., three flaps as schematically shown in FIG. 6a) for functional replacement of the native heart valve. The tubular body 30 may be provided with an outer circumferential groove 45. The outer circumferential groove 45 may be open to the radial outside of the tubular body 30. The circumferential groove 45 may define a groove bottom 46. The outer circumferential groove 45 may define a channel 47 which is defined itself by the groove bottom 46 and axially (in axial direction of the tubular body 30) opposite side walls 48, 49. The groove bottom 46 may separate the tubular body 30 into first and second body sections 31, 32. The circumferential groove 45 may extend around a whole circumference of the tubular body 30 or may only extend partially around a circumference of the tubular body 30. The outer circumferential groove 45 may be a continuous, that is non-interrupted, groove, or may be an interrupted groove 45 having, for example, two or more circumferential groove portions 45 provided, for example, on the same axial level of the tubular body 30 that are interrupted by areas in which no recessed portion, which may provide the groove portion, is formed. The circumferential groove 45 may be located at an axial distance (along axis 35) from the axial ends of the tubular body 30, i.e. the circumferential groove 45 may be spaced apart in an axial direction from end portions of the tubular body 30.

As shown in FIG. 1, the first body section 31 may be the part of the tubular body 30 that is located above (e.g., proximal from) the circumferential groove 45, and the second body section 32 may be the part of the tubular body 30 that is located beneath (e.g., distal from) the circumferential groove 45. Both of the first and second body sections 31, 32 may have a generally cylindrical shape. According to embodiments, the first body section 31 may have a generally conical or expanding shape along the axis of the tubular body, with its cross-section diameter increasing from the groove 45, and the second body section 32 may be generally cylindrical. According to embodiments, both of the first and second body sections 31, 32 may have a conical shape along the axis of the tubular body, with their respective cross-sectional diameters increasing from the groove 45. Additionally, the outflow end of the tubular body may include a frustoconical shape that slopes radially outward from the preformed groove toward the outflow end when the outflow end, but not the inflow end, has been released from a delivery catheter.

According to embodiments, the cross sections (along axis 35) of sections 31 and/or 32 may be or contain non-circular shapes such as elliptical or D-shaped cross sections. In addition, the direction of curvature in the axial profile (seen in an axial section along the tubular body 30) between the groove 45 and the first body section 31 and/or between the groove 45 and the second body section 32 may change (from concave curvature of the groove 45 to a convex curvature at the transition between groove 45 and first and/or second body section 31, 32). The axially opposite side walls 48, 49 of the groove 45 may be part of the first and second, respectively, body sections 31, 32 and may axially delimit the first and second, respectively, sections 31, 32 towards the channel 47 of the groove 45, as it is shown, e.g., in FIG. 8. A radial diameter of the first body section 31 (e.g., at an end portion that is opposite to the second body section 32) of the tubular body 30 may be larger than any diameter of the second body section 32. This may allow one to more efficiently fix the prosthesis 1 in the connection channel 10 as the first body section 31 having a larger diameter may provide a better hold of the prosthesis 1 in the connection channel 10 by providing a friction and/or (mere) form fit (e.g., caused by the first body section 31 being located in the atrial chamber 15 and having a diameter larger than a diameter of the connection channel 10).

Figure 12:
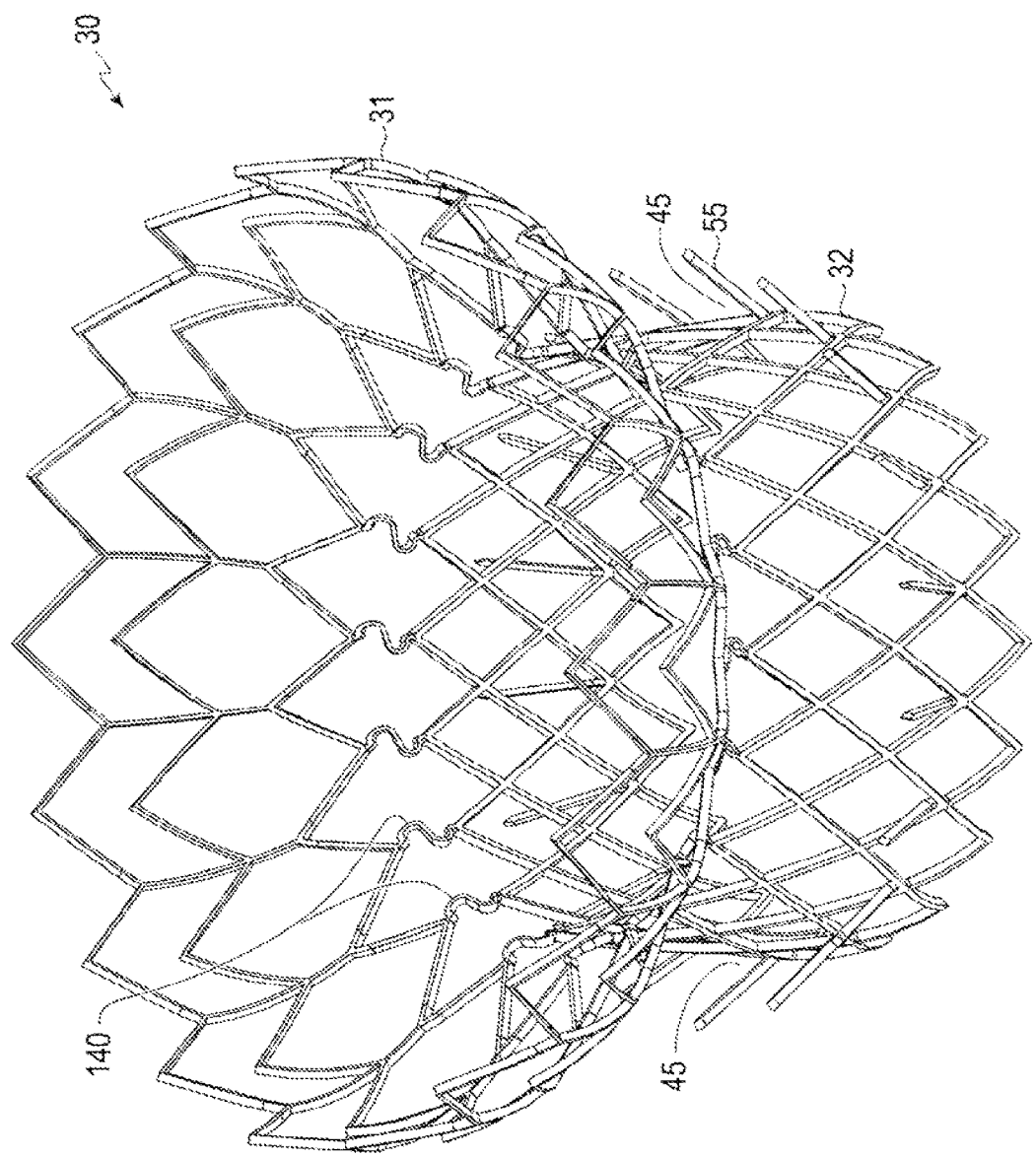

As shown in FIG. 12, the tubular body 30 may include one or more decorrelation portions 140 configured to dissociate axial and radial movements between an inflow end and an outflow end of the tubular body 30. For example, the decorrelation portions 140 may dissociate movements between first body section 31 and second body section 32 (FIG. 1). The decorrelation portions may be disposed adjacent to and outside the circumferential groove 45. As show in FIG. 12, the circumferential groove 45 may be disposed between the decorrelation portions 140 and the outflow end of the tubular body 30, and for example, between the valve 40 and the inflow end. In some embodiments, the decorrelation portions may each include flexible "S" shaped portions or a flexible material, such as polyester fabric. In other embodiments, the decorrelation portions 140 may include a combination of such components. The decorrelation portions are generally configured to stretch or compress in reaction to movement in the outflow or inflow ends. Thus, because the decorrelation portions stretch and/or compress, movement from one end of the tubular body does not translate/communicate to the other end of the tubular body. In this manner, movement in the ends of the tubular body do not correlate with one another.

Further, the valve prosthesis 1 may comprise a first plurality of projections 50 and a second plurality of projections 55. The projections 50, 55 may extend from the first and second sections 31, 32, respectively, in opposite axial directions, that is at least with an extension component or an extension vector in a direction along the axis 35 (e.g., the longitudinal axis 35) of the tubular body 30. Accordingly, the first projections 50 and the second projections 55 extend generally towards each other, whereby they may not extend exactly or in line towards each other, but with an extension vector. The projections 50, 55 may extend substantially parallel to the axis 35 of the tubular body 30 or may also extend in a (lateral) angle γ to the axis 35 of the tubular body 30, wherein the (lateral) angle γ extends tangential to the circumference of the tubular body 30, as it is shown, e.g., in FIG. 2a.

Figure 11A:
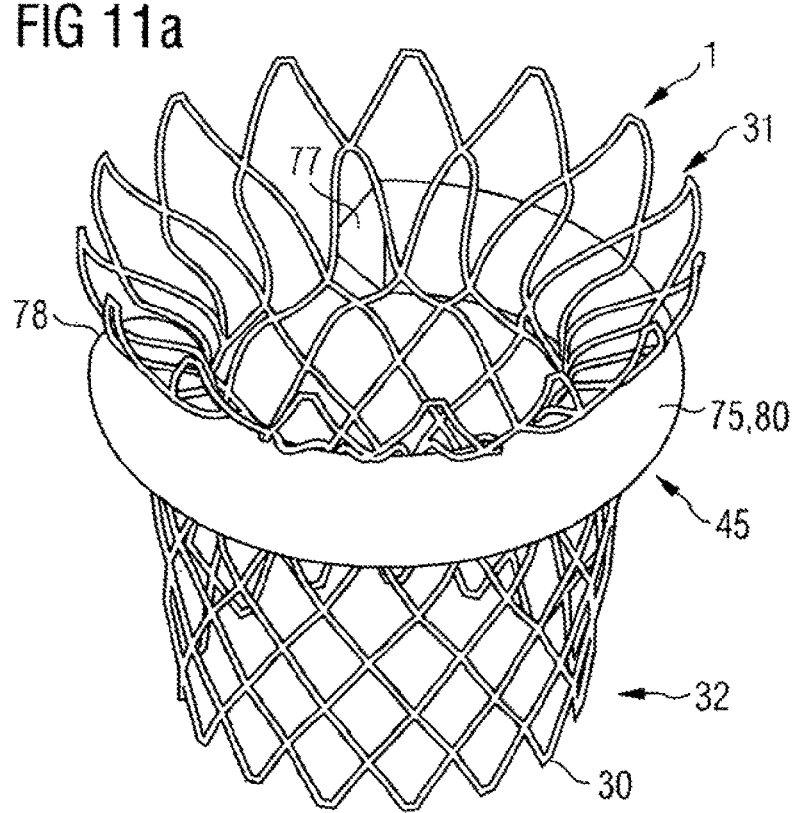
Figure 11B:
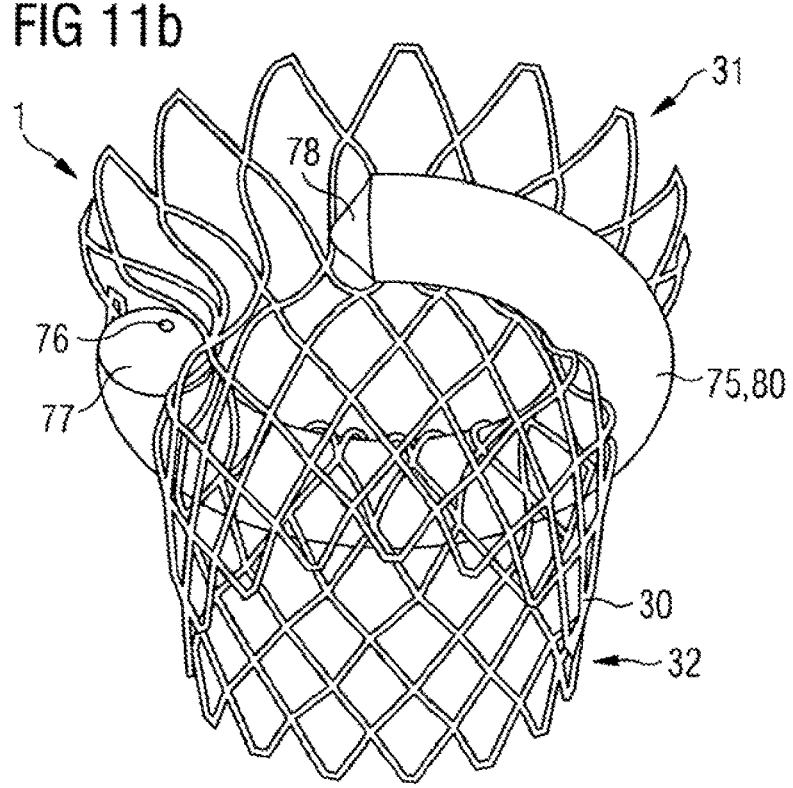
Figure 11C:
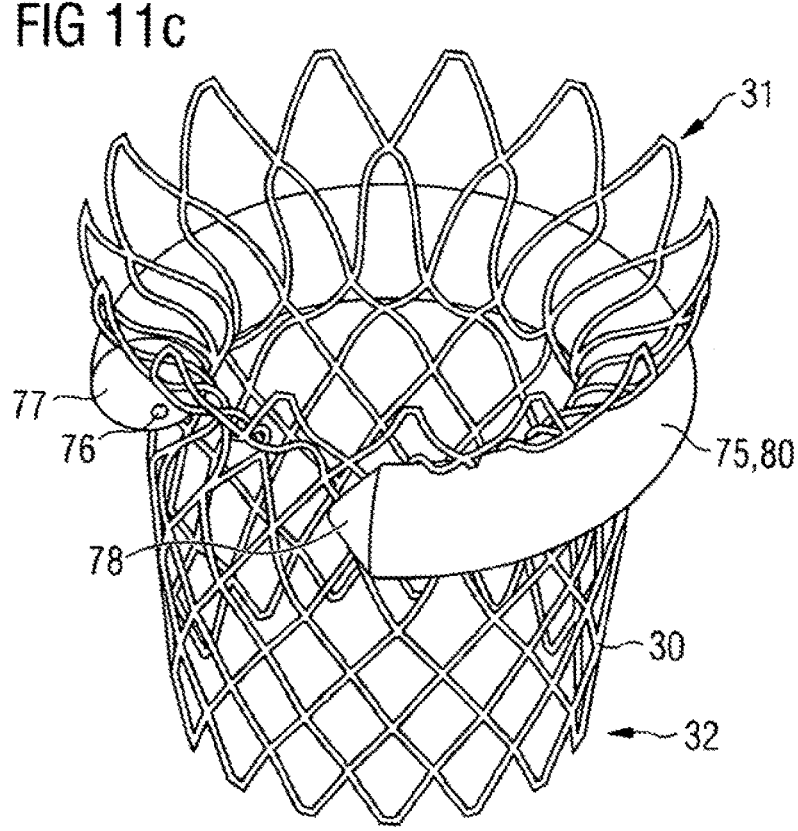
Figure 11D:
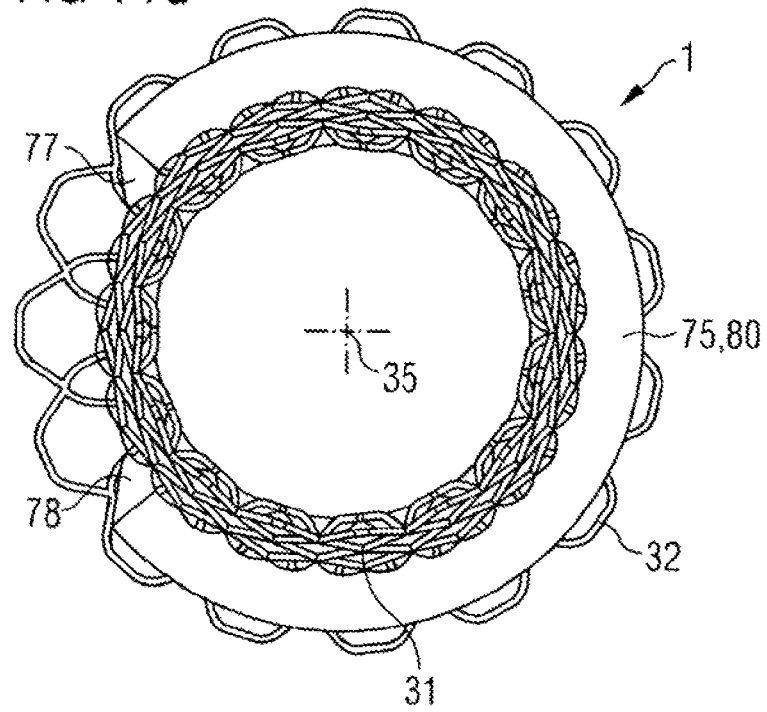

The valve prosthesis 1 may comprise one plurality of projections 50, 55 that may extend from the first or second sections 31, 32 in an axial direction of the tubular body 30 and may overlap the circumferential groove 45. With reference to, e.g., FIGS. 11a-c, the valve prosthesis 1 may not comprise any projections 50, 55, and the circumferential groove 45 may be provided with (e.g., integrally formed on) the tubular body 30.

Figure 13A:
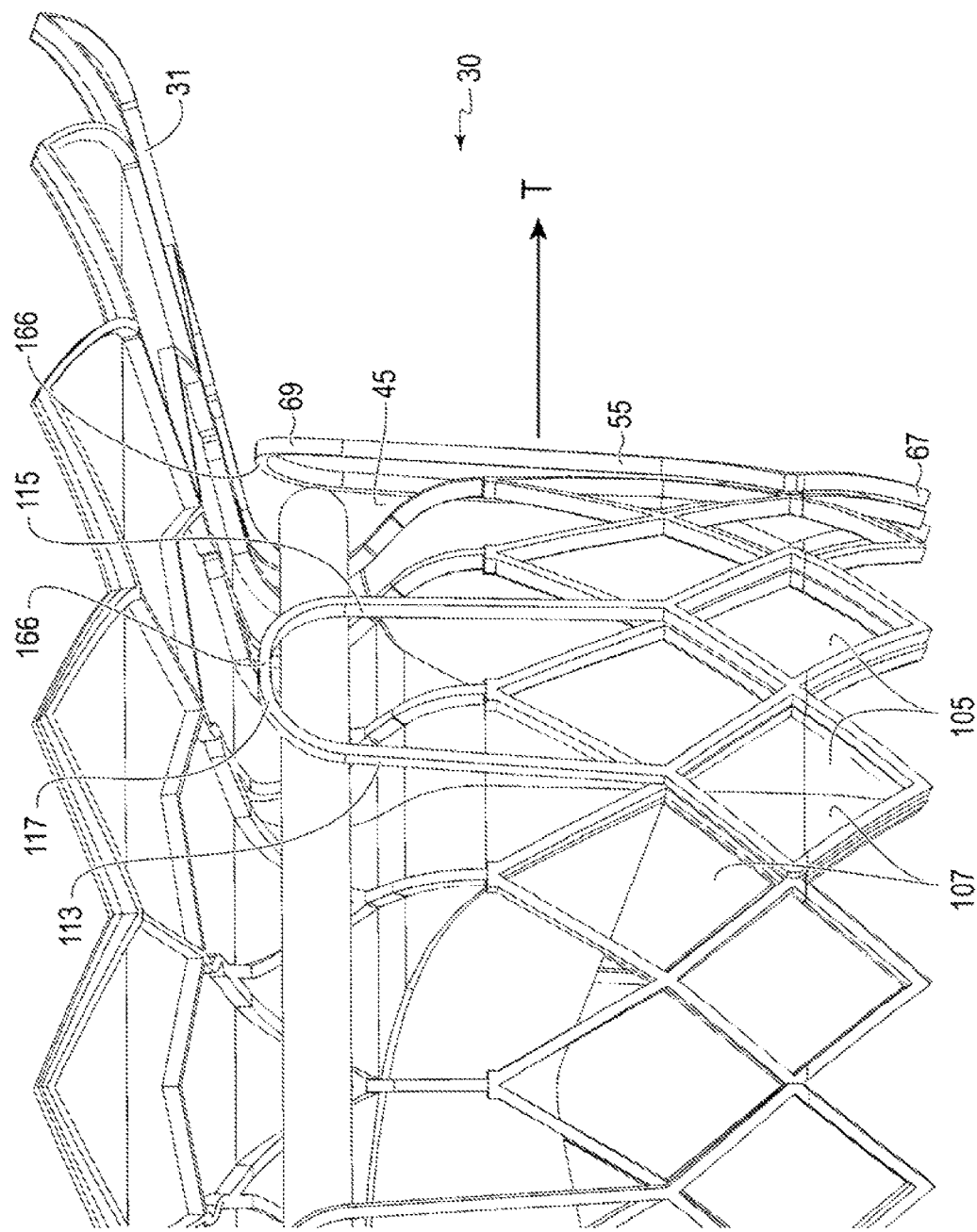
Figure 13B:
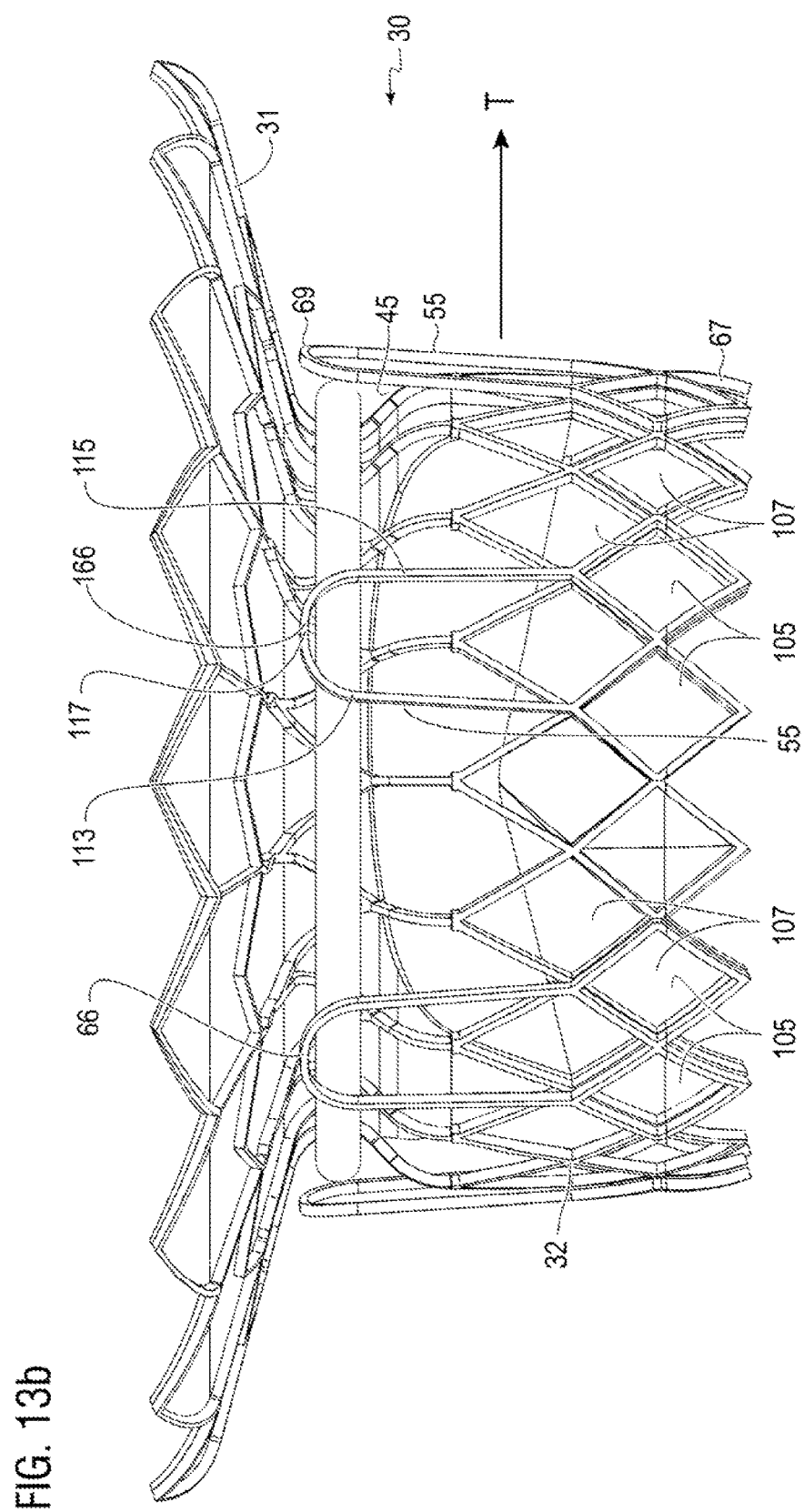

The projections of the first plurality of projections 50 each may have a first end 67 and a second end 69 (FIGS. 13a and 13b). The first end 67 may be connected to the tubular body 30 and the second end 69 may form a free end unattached to the tubular body 30. For example, the first plurality of projections 50 may include free ends 60 and the second plurality of projections 55 may include free ends 65 (FIG. 1). The free ends 60, 65 of the first and second pluralities of projections 50, 55 may be arranged so as to overlap the outer circumferential groove 45. That is, the free ends of the first and second pluralities of projections 50, 55 are arranged at an axial level of the groove 45 so as to overlap the groove 45. The first and second pluralities of projections 50, 55 as such may at least partially or completely overlap the groove 45 along their extension.

The first 50 and second 55 pluralities of projections may extend in a radial distance radially outwards of the bottom 46 of the groove 45 so that a hollow (circumferential) chamber 66 is defined between the groove bottom 46 and the first and second pluralities of projections 50, 55 in the channel 47. The opposite side walls 48, 49 may further define the hollow chamber 66 in the axial direction of the tubular body 30. Hence, the hollow chamber 66 may be confined radially by the pluralities of projections 50, 55 and the groove bottom 46 and axially by opposite sidewalls 48, 49 (e.g., top- and bottom-walls) of the groove 45.

Figure 1A:
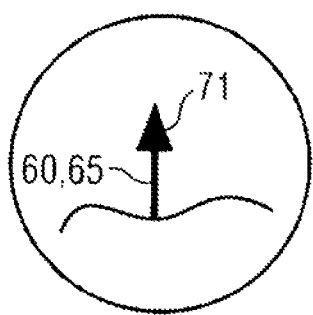
FIG. 1a shows a detail of a free end of a projection of the valve prosthesis according to embodiments.
Figure 14:
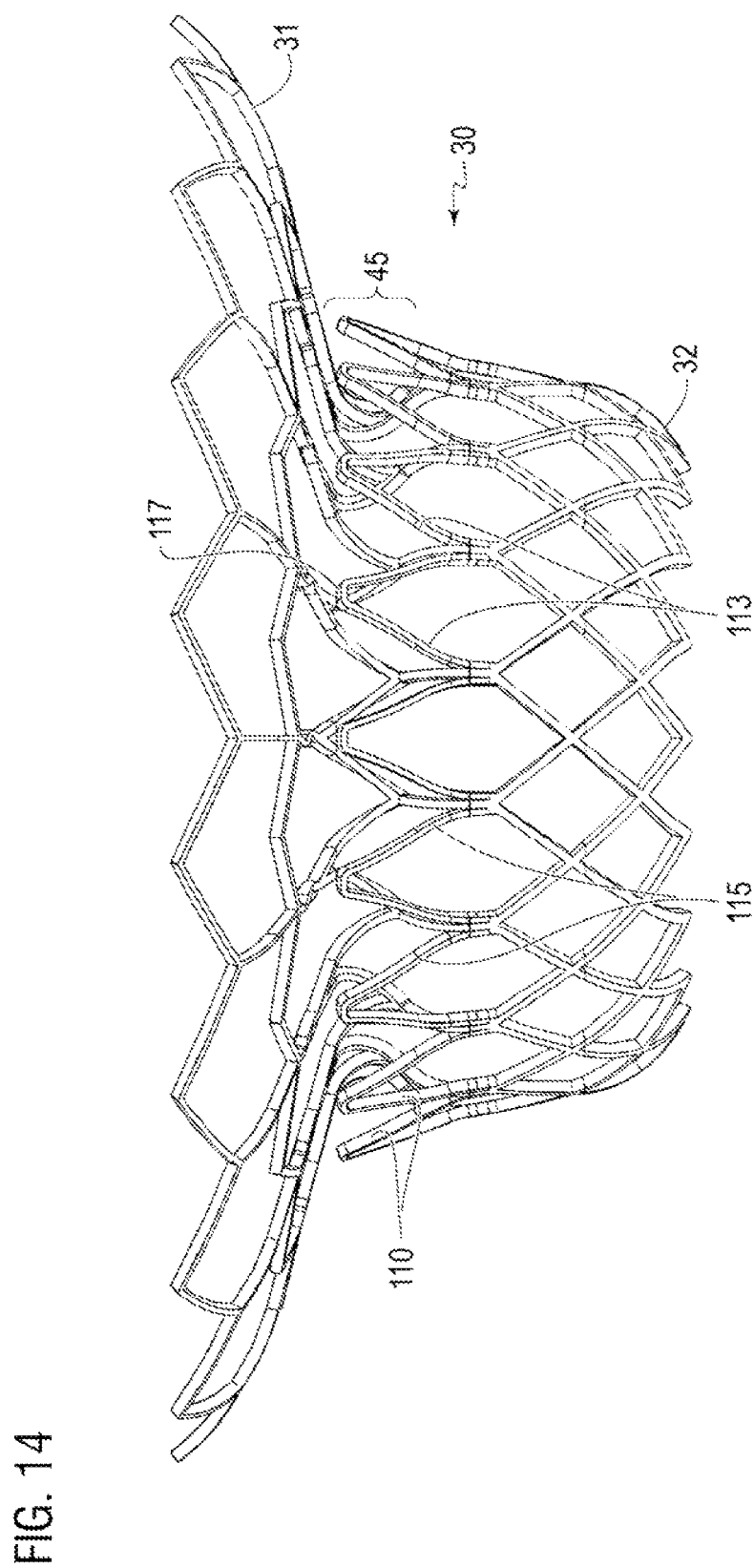
Figure 16A:
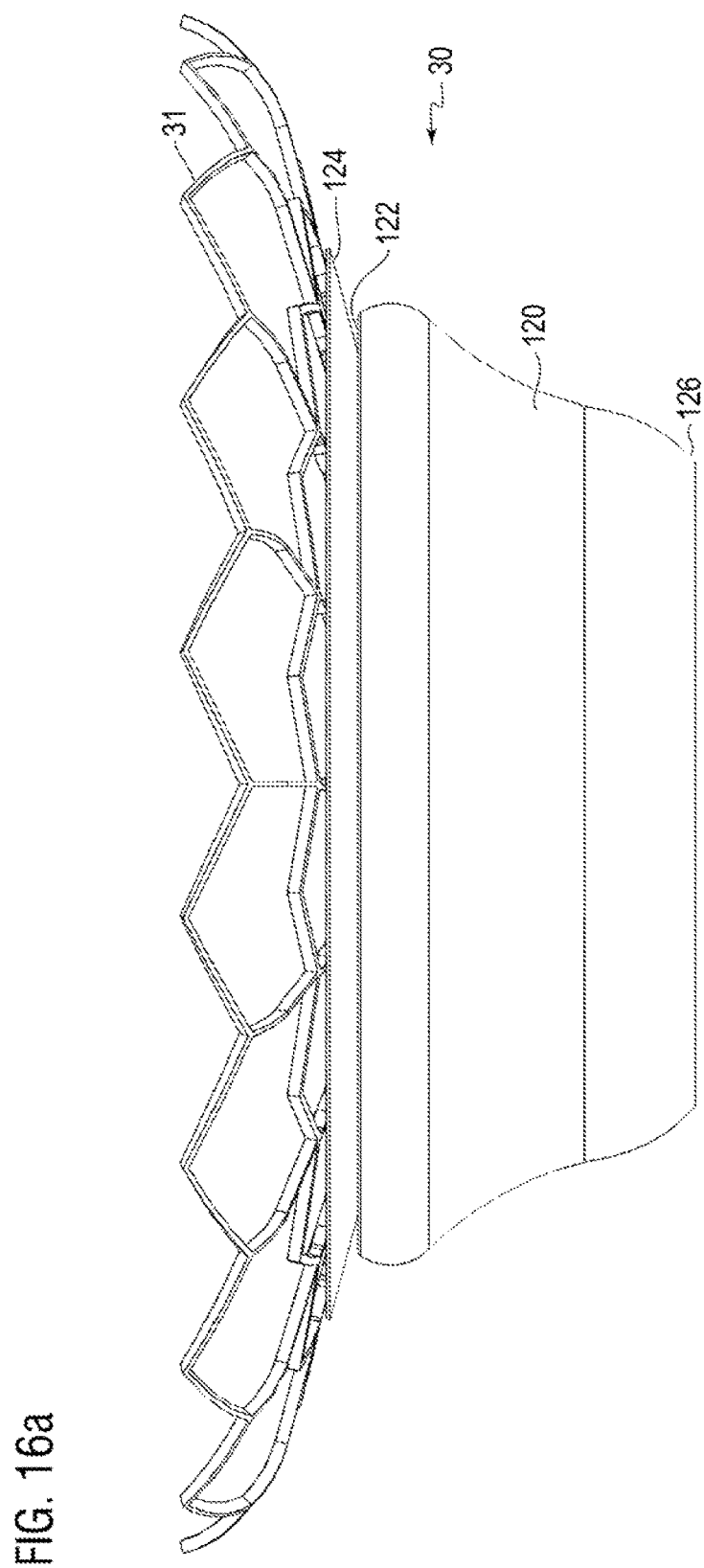
Figure 16B:
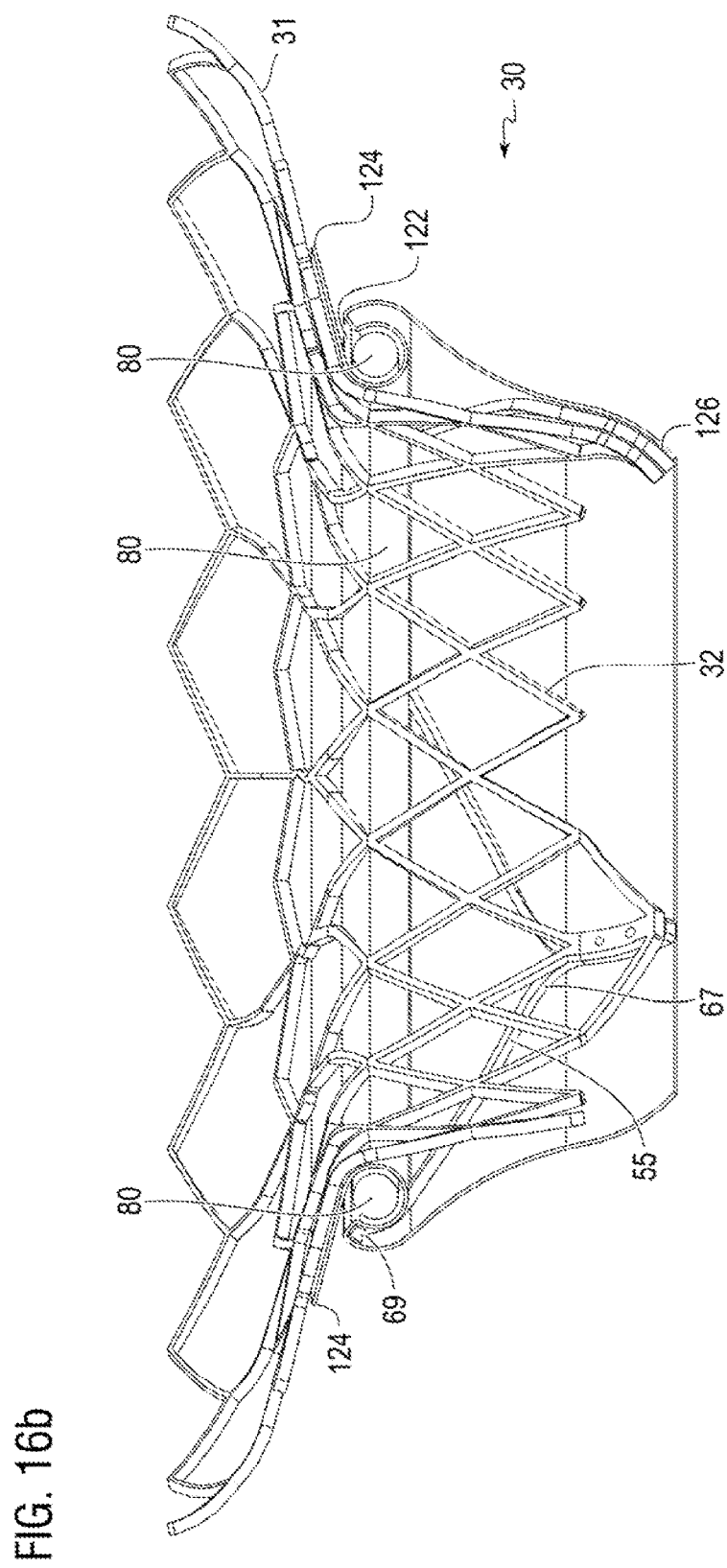
Figure 19:
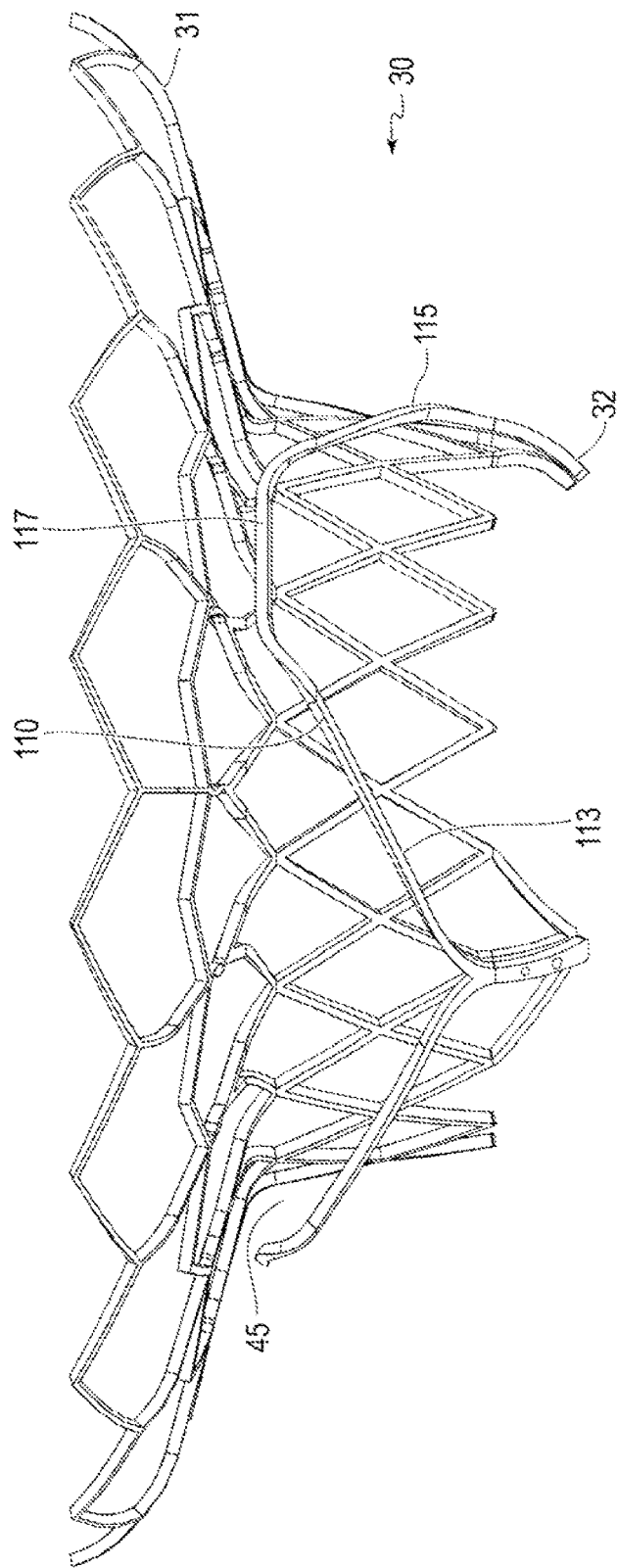

In embodiments, the second ends 69 of projections 50, 55 may include barbs configured to penetrate tissue (FIG. 1a). In other embodiments, the second ends 69 may include blunt ends configured not to penetrate tissue, for example substantially flat ends 166 extending in a direction substantially parallel to a tangent T of the tubular body 30 (FIGS. 13a and 13b), or a plurality of struts 110 forming rounded (e.g., rounded corner triangle) configurations (FIG. 14). In yet additional embodiments, some or all of projections 50, 55 may include barbs, blunt ends, and/or rounded configurations. Transcatheter valve prosthesis 1 may include, in embodiments, the first plurality of projections 50 and/or the second plurality of projections 55. In these embodiments the first plurality of projections 50 or the second plurality of projections 55 may extend a sufficient distance so that the hollow chamber 66 is defined between the groove 45 and the first plurality of projections 50 and/or the second plurality of projections 55. Alternatively or additionally, the first plurality of projections 50 and/or the second plurality of projections 55 may define the circumferential groove 45 between the tubular body 30 and the projections 50 and/or 55, e.g., without indenting of the tubular body. For example, as shown in FIGS. 16b and 19, circumferential groove 45 is defined between the tubular body 30 and the second plurality of projections 55. A method of using a transcatheter valve prosthesis 1 may comprise positioning it in the connection channel wall structure 25 of a heart and then inserting tissue that is adjacent to the circumferential groove 45, of the connection channel wall structure 25 into the circumferential groove 45, for example to be placed radially below the first and second plurality of projections 50, 55. The tissue can then be held in place in the circumferential groove 45, for example by the first 50 and/or second plurality of projections 55, which, if, for example, provided with acute or sharpened ends, may penetrate into the tissue which from its position below may be biased back to its initial radial position. The prosthesis 1 may be positioned such that its outer circumferential groove 45 is at the level of the annulus of the circumferential wall structure 25 or adjacent thereto towards the side of the ventricular chamber 20. By the first and second plurality of projections 50, 55 keeping the tissue within the groove 45, the transcatheter valve prosthesis 1 can be positioned and fixed relative to the heart. Further, since the first and second plurality of projections 50, 55 axially extend towards each other, the prosthesis is safely and reliably prevented from being axially pushed out of the connection channel 10 by the pumping activity of the heart. The first 50 and/or the second 55 plurality of projections may keep the tissue of the connection channel wall structure 25 in the circumferential groove 45 by perforating it (e.g., transfixing it, e.g., skewering it) and/or by an interference fit. The tissue that is held in the circumferential groove 45 may also (partially or fully) seal the transcatheter valve prosthesis 1 against the interior of the connection channel 10 so that blood, e.g., pressurized blood, can only flow through the tubular body 30 (and the artificial heart valve 40 therein) but can not bypass the tubular body 30 on its exterior side (i.e., between the exterior of the tubular body 30 and the interior of the connection channel wall structure 25). In this respect, the inner and/or outer circumferential surface of the tubular body 30 may additionally be provided with an impermeable layer, for example in the form of a liner 33b.

The prosthesis 1 may be located in the connection channel 10 so that the circumferential groove 45 is located on the ventricular side of the annulus of a natural valve, e.g., having a distance from the natural valve annulus, i.e., the circumferential groove 45 may be a sub-annular circumferential groove and/or the prosthesis 1 may be a sub-annular-prosthesis 1. The prosthesis 1 may be adapted to be a sub-annular prosthesis. That is, the tubular body 30 may have a transverse dimension (also referred to as diameter herein) at an axial level (with respect to axis 35) that is smaller than a transverse dimension of a natural valve annulus, and/or transverse dimension and/or axial lengths of the tubular body may be suitable so that the first body section 31 may be located in an atrial chamber 15 and that the second body section 32 may be located in the connection channel 10 with the groove 45 being located on a ventricular side of the natural valve annulus having a distance to said annulus.

Only one circumferential groove 45 as described above may be provided on the tubular body 30. However, an elongated prosthesis 1 having two or more circumferential grooves 45 may be provided, wherein a respective set of first and second pluralities of projections 50, 55 as described above may be arranged and assigned to the respective one of the two or more grooves 45. The groove 45 or the respective groove may be formed by the first and second body sections 31, 32 of the tubular body 30 as such, wherein the projections 50 and/or 55 may or may not be involved in forming the (respective) groove 45 as such. There may also be embodiments (see further below), in which the projections 50 and/or 55 at least partially form the groove 45, for example on the side of the tubular body 30 that is proximal to the ventricular chamber 20.

The tubular body 30 may comprise or may be a mesh-type body having elongate mesh or grid elements 33 (e.g., stent struts 107 and/or projections) crossing each other at crossings 34. The mesh elements 33 may be formed from wires or, for example, a laser-cut tube comprising steel and/or a superalloy and/or a shape memory alloy (e.g., nitinol) and/or nickel and/or titanium and/or precious metals (e.g., gold) and/or alloys comprising the aforementioned. The mesh elements 33 may also comprise other alloys or may be made from organic material, e.g., polymers. The mesh elements 33 may, e.g., be made from polyvinyl-chloride and/or polystyrene and/or polypropylene or another polymer. The tubular body 30 may be from a shape-memory material which expands when experiencing usual body temperature. The tubular body 30 may be self-expandable. The tubular body 30 may also be not self-expandable, but expandable by a balloon or another expansion mechanism. Correspondingly, the tubular body 30 may be compressible to be insertable via the catheter and may then be expandable when appropriately positioned within the connection channel wall structure 25. The tubular body 30 may comprise the above-mentioned liner 33b (c.f. FIG. 6a) attached to the mesh elements 33 made from the same or made from different materials. The liner 33b may be disposed on an interior side or an exterior side of the mesh elements 33 and/or tubular body 30 and may cover the circumference of the tubular body 30 fully or only partially in axial direction 35 and/or in circumferential direction.

The circumferential groove 45 of the tubular body 30 and/or the projections of the first and/or the second plurality of projections 50, 55 may interact with the connection channel wall structure 25 so as to fix the valve prosthesis 1 with respect to the channel wall structure 25 and the connection channel 10. Tissue of the channel wall structure 25 may be "caught" in the circumferential groove 45 and be held in place by the free ends 60, 65 of the first and/or the second plurality of projections 50, 55, which may serve as hook elements. The tissue of the channel wall structure 25 may be perforated by the free ends 60, 65 and thereby held more firmly in the circumferential groove 45 of the tubular body 30, wherein the tissue may also be held in the groove 45 by an interference and/or clamping fit between the projections 50 and/or 55 (or part thereof) and the tissue of the connection channel wall structure 25. In order to allow the first and/or second plurality of projections 50, 55 to penetrate the tissue of the circumferential connection channel wall structure 25, which has been forced into the groove, the free ends of a plurality or of each of the first 50 and/or second 55 pluralities of projections may be an acute or sharpened end. The projections of the first and/or second plurality of projections 50, 55 each or some thereof may be pins.

Figure 1B:
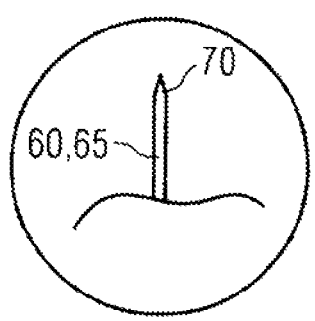
FIG. 1b shows a detail of a free end of a projection of the valve prosthesis according to embodiments.

With further reference to FIG. 1b, the free ends 60, 65 of the first and/or the second plurality of projections 50, 55 may be conical ends 70 so as to be able to perforate tissue of the connection channel wall structure 25. According to embodiments, the free ends 60, 65 of the first and/or the second plurality of projections 50, 55 may also be blunt. The free ends 60, 65 and/or the first and/or second plurality of projections 50, 55 may be pin-shaped.

Some or all of the free ends 60, 65 of the projections 50, 55 may comprise barbs or hooks 71 as shown in FIG. 1a. The hooks 71 may serve to perforate tissue of the connection channel wall structure 25 and prevent the tissue from slipping off the free ends 60, 65. Thereby tissue that is perforated by barbs or hooks 71 disposed on a free end 60, 65 is unable to slip from the free end 60, 65 resulting in tissue from the heart valve connection channel wall structure 25 being caught even more reliably in the circumferential groove 45. Some or all of the free ends 60, 65 may be blunt or may have conical ends 70 or comprise barbs or hooks 71. The first 50 or second 55 plurality of projections may comprise different types of free ends 60, 65 according to the anatomical conditions, but may also comprise the same type of free ends 60, 65.

The free ends 60, 65 and/or the first 50 and second pluralities 55 of projections may be arranged in different axial and/or radial positions and orientations with respect to each other. With reference to FIGS. 1 and 6a, each projection of the first plurality of projections 50 may have the same circumferential angular distance a (that is an angular distance between two radial directions extending from longitudinal axis 35 of the tubular body 30) from each other, i.e. the projections 50 may be equally circumferentially spaced. However, the projections of the first plurality of projections 50 may also have different angular distances a from each other, i.e. be not spaced evenly around a circumference of the tubular body. Although not shown in FIGS. 6a-c, similarly, each projection of the second plurality of projections 55 may have the same angular distance from each other, i.e. be spaced equally around a circumference of the tubular body 30. However, the projections of the second plurality of projections 55 may also have different circumferential angular distances a from each other, i.e. be not spaced evenly around a circumference of the tubular body.

Figure 3:
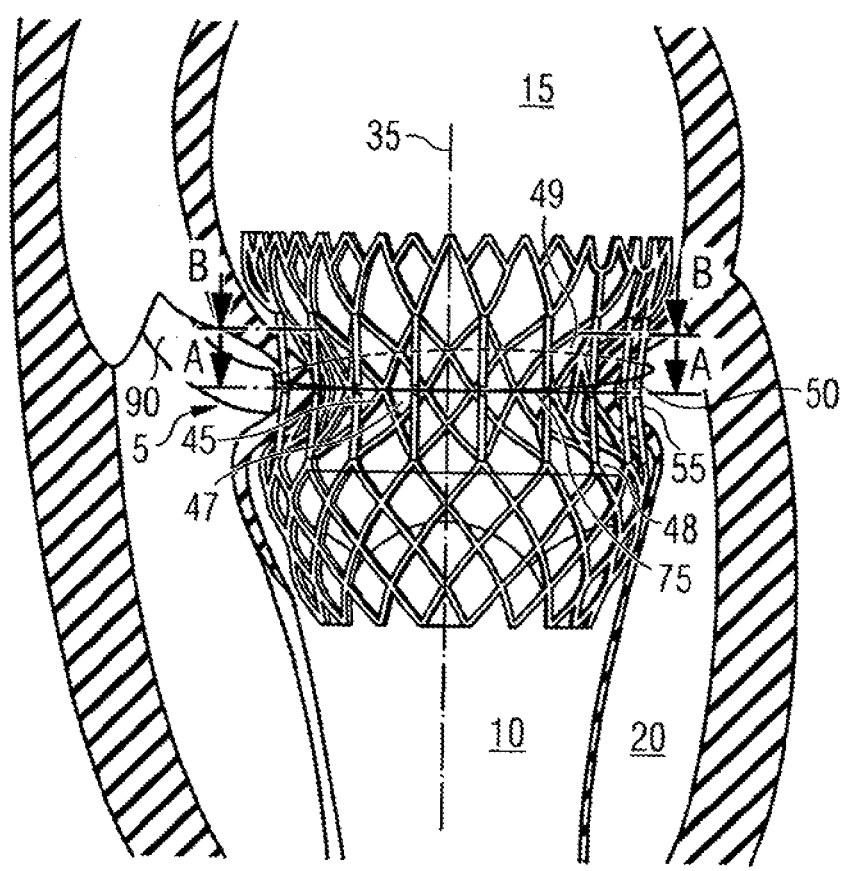
FIG. 3 shows schematically a transcatheter valve prosthesis comprising an elongate outer member according to embodiments located in a connection channel of a human heart.

The first plurality of projections 50 may be arranged with respect to the second plurality of projections 55 on the tubular body 30 in a way that each projection of the first plurality of projections 50 is substantially on the same radial level (that is the same radius, e.g., R2) as a projection of the second plurality of projections 55 (as it is shown e.g., in FIGS. 1 and 3). On the other hand, some or each of the projections of the first plurality of projections 50 may be arranged on a different radius than a projection of the second plurality of projections 55, for example such that the first plurality of projections 50 may each be on a same radius, and the second plurality of projections 55 may each be on a same radius.

With, for example, reference to FIGS. 1 and 3, the first plurality of projections 50 and the second plurality of projections 55 may extend so as to be aligned or coaxial to each other. The first plurality of projections 50 may also not be aligned with the second plurality of projections 55. For example, the first plurality of projections 50 may themselves extend substantially parallel to each other or may not, and the second plurality of projections 55 may themselves extend substantially parallel to each other or may not.

Figure 2:
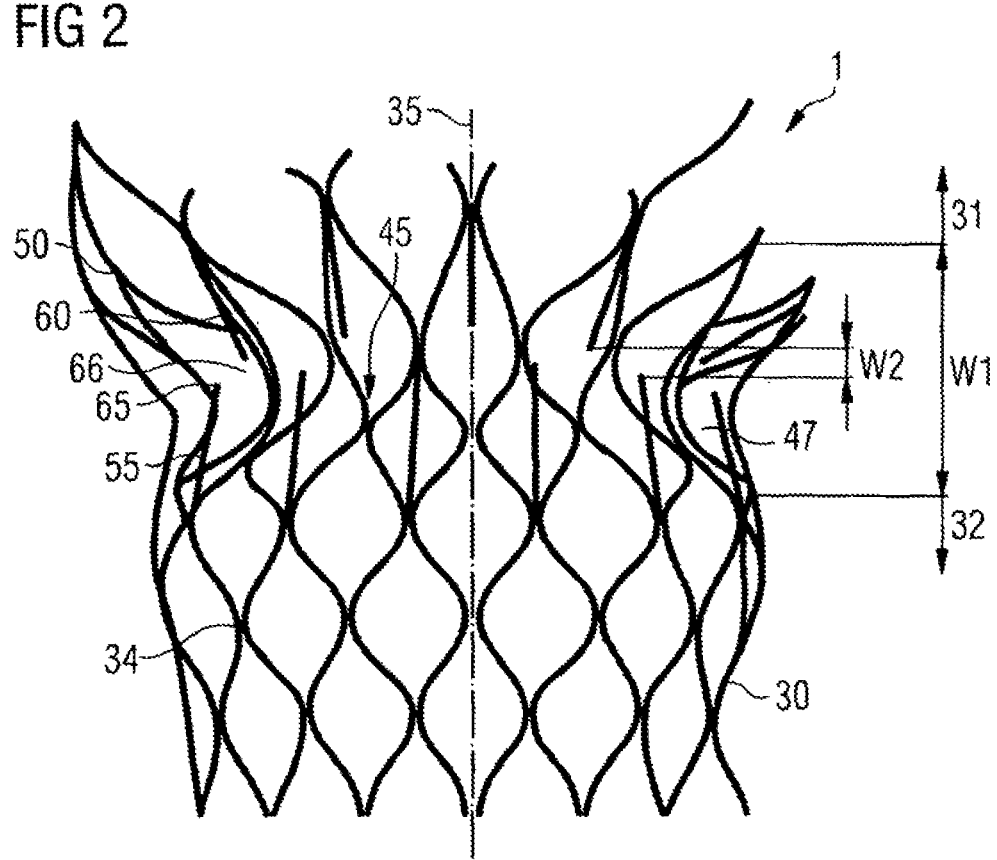
FIG. 2 shows a transcatheter valve prosthesis according to embodiments, FIG. 2a schematically shows extension angles of projections according to embodiments.
Figure 4:
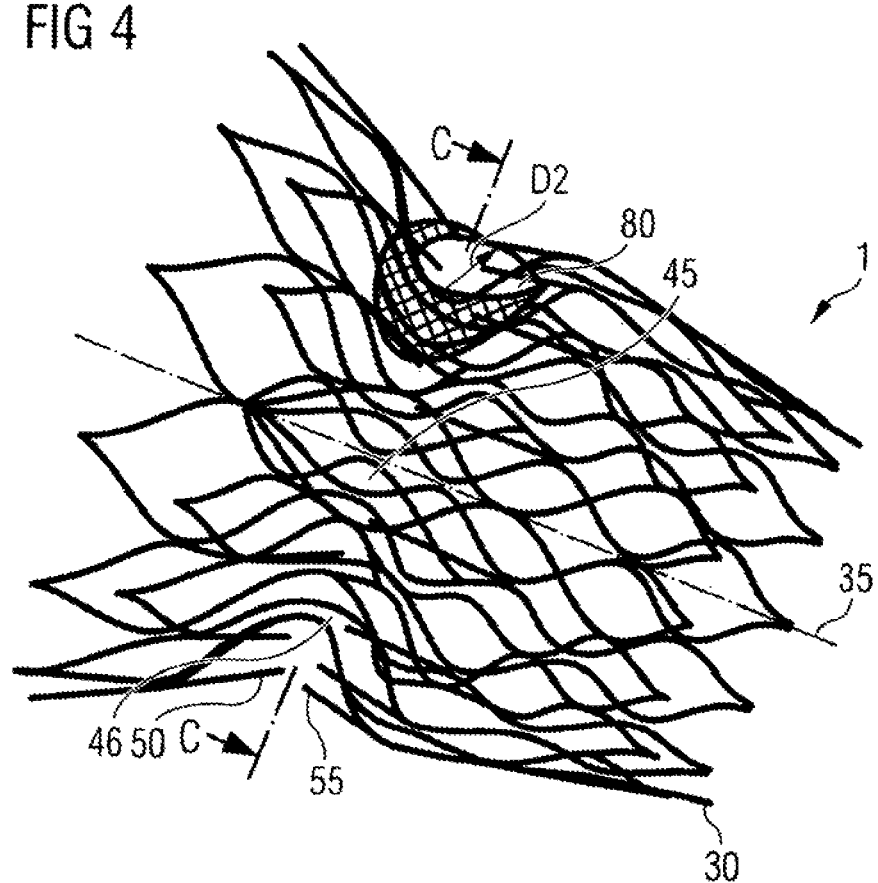
FIG. 4 shows a transcatheter valve prosthesis including a clamping member according to embodiments.

With, for example, reference to FIGS. 2 and 4, the first and second pluralities of projections 50, 55 may be arranged in circumferential direction in an alternating manner, wherein for example each first projection 50 is circumferentially between two second projections 55 (and the other way round). There may also be other appropriate circumferential arrangement patterns for the first and second pluralities of projections 50, 55, wherein, for example, sets of first projections 50, of for example one, two, three, four, or more first projections 50, are arranged between sets of second projections 55, of, for example, one, two, three, four or more second projections 55.

The number of projections of the first plurality of projections 50 and the number of projections of the second plurality of projections 55 may be, for example, in a range of three to five, or eight to ten, fifteen to twenty, thirty to one hundred or more, or may be any other number. The first plurality of projections 50 may comprise the same number of projections or another number of projections as the second plurality of projections 55 or vice versa.

Figure 9A:
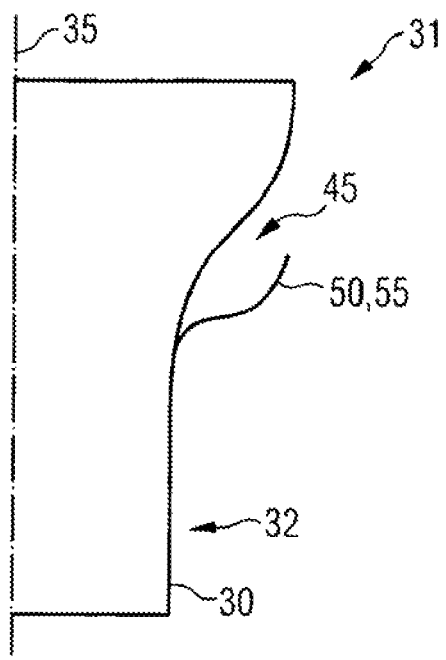
FIG. 9a shows a tubular body of a transcatheter valve prosthesis.
Figure 9B:
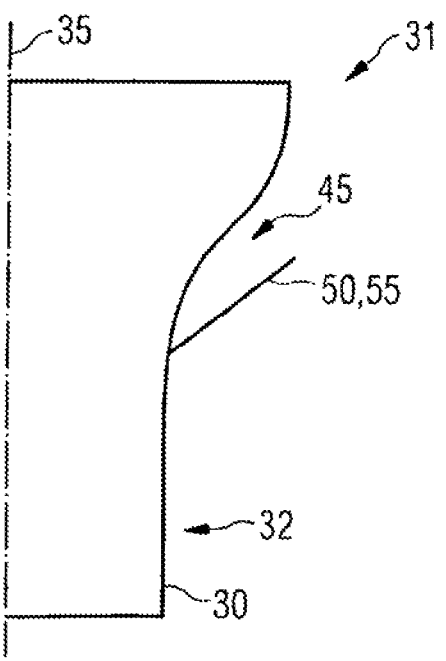
FIG. 9b shows a tubular body of a transcatheter valve prosthesis, FIG. 10a schematically shows a transcatheter valve prosthesis including an outer member, FIG. 10b schematically shows a transcatheter valve prosthesis including an outer member, FIG. 10c schematically shows a transcatheter valve prosthesis including an outer member, FIG. 11a schematically shows the transcatheter valve prosthesis including an elongate outer member according to embodiments, FIG. 11b schematically shows the transcatheter valve prosthesis including an elongate outer member according to embodiments, FIG. 11c schematically shows the transcatheter valve prosthesis including an elongate outer member according to embodiments, FIG. 11d schematically shows the transcatheter valve prosthesis including an elongate outer member according to embodiments, FIG. 12 schematically shows the transcatheter valve prosthesis according to embodiments, FIGS. 13a and 13b schematically show the transcatheter valve prosthesis according to embodiments, FIG. 14 schematically shows the transcatheter valve prosthesis according to embodiments, FIGS. 15a, 15b, and 15c schematically show the transcatheter valve prosthesis and insertion member, FIGS. 16a and 16b schematically show the transcatheter valve prosthesis according to embodiments, FIGS. 17a, 17b, 17c, 17d, and 17e schematically show the transcatheter valve prosthesis according to embodiments, FIG. 18 schematically shows the transcatheter valve prosthesis according to embodiments, FIG. 19 schematically shows the transcatheter valve prosthesis according to embodiments, FIG. 20 schematically shows the clamping member according to embodiments, FIG. 21 schematically shows the clamping member according to embodiments, FIG. 22 schematically shows the clamping member according to embodiments, FIG. 23 schematically shows the clamping member according to embodiments, FIG. 24 schematically shows the clamping member according to embodiments, FIGS. 25a, 25b, and 25c schematically show the clamping member according to embodiments, FIG. 26 schematically shows the transcatheter valve prosthesis according to embodiments, and FIG. 27 schematically shows the transcatheter valve prosthesis according to embodiments.

The projections of the first plurality of projections 50 and/or the projections of the second plurality of projections 55 may extend from the tubular body 30 from positions where mesh elements 33 of the tubular body 30 are crossing with each other at the crossings 34. This may improve the mechanical stability of the interconnection of the tubular body 30 with the projections 50, 55. The projections 50, 55 may, e.g., be welded, soldered and/or braided to the tubular body 30. They may be sutured, bonded or glued to the tubular body 30. As an alternative or additionally, the projections 50, 55 may also be monolithically integrally formed with the tubular body 30. That is, with reference to, e.g., FIGS. 9a and 9b, the projections 50,55 (or any one or both of the pluralities of projections) may be formed by mesh elements 33 that are not connected to another mesh element 33 at a crossing 34 but are projecting from the tubular body 30 (e.g., caused by bending the mesh element 33) in a radial and/or axial direction with respect to longitudinal axis 35 so as to form a projection 50, 55. Further, projections 50, 55 (e.g., monolithically integrally formed by mesh elements 33 or provided separately and connected with the tubular body 30) may form the circumferential groove 45 by projecting radially and axially from the tubular body 30 with respect to its longitudinal axis 35. Accordingly, by facing away from the tubular body 30, the projections may define a circumferential groove 45 on the tubular body 30. The circumferential groove 45 may be further defined by a generally conical or similar shape of a body section (e.g., first body section 31 and or second body section 32) of the tubular body 30 that has a cross-sectional diameter that is increasing from the groove 45 in a direction of longitudinal axis 35. As seen e.g., in FIGS. 9a and 9b, the generally conical shape of a body section 31, 32 may accordingly interact with the projections 50, 55 which are projecting from the tubular body 30 so as to further define the circumferential groove 45. FIG. 9a shows projections 50, 55 that define a circumferential groove 45 by projecting first in a substantially radial direction relative to the longitudinal axis 35 and then in a substantially parallel direction to the longitudinal axis 35 when seen from the point from which the projections extend from tubular body 30. FIG. 9b shows projections 50, 55 that extend generally rectilinearly to define the circumferential groove 45. The projections 50, 55 may be made from the same materials that were described above with reference to the tubular body 30, e.g., super alloys, e.g., shape memory alloys (like nitinol) or steel or titanium (or alloys comprising titanium) or organic material like polymers, or the projections may be made from different material or materials.

In embodiments, the first end 67 of the first plurality of projections 50 and/or the second plurality of projections 55 may include one or more first apertures 105 substantially aligned with second apertures disposed between stent struts 107 of the tubular body 30 (FIGS. 13a and 13b). The first apertures 105 may include various configurations including, for example, square, circular, and triangular. Additionally, the first apertures 105 may be larger than, smaller than, or of approximately equal size to the second apertures disposed between the stent struts 107. The second end 69 of the first plurality of projections and/or the second plurality of projections 55 may also include a match circumferential curvature of stent surface that does not include an aperture. In the embodiment of FIGS. 13a and 13b, the second ends 69 form substantially flat ends 166 and extend in a direction parallel to a tangent of the tubular body 30, and therefore second ends 69 are configured so as not to cause trauma to the surrounding tissue (e.g., Tangent T, as indicated on FIGS. 13a and 13b).

As discussed above, in embodiments, the first plurality of projections 50 and/or the second plurality of projections 55 may include blunt ends configured not to penetrate the tissue. For example, the struts 110 may each include a first strut 113 and a second strut 115 joined through connector 117. As shown in FIG. 14, for example, the first struts 113, the second struts 115, and the connector 117 together may form rounded triangle configurations. In alternate embodiments, the struts 110 may comprise various configurations, for example, rectangular, rounded, elliptical, or a combination of these configurations, for example, the planar projection shown in FIGS. 13a and 13b. In the embodiment of FIGS. 13a and 13b, for example, each connector 17 forms substantially flat end 166. Additionally, the struts 110 may include asymmetrical and/or irregular configurations. For example, as shown in FIG. 19, first struts 113 may not be symmetrical with second struts 115 such that the first and second struts 113, 115 each include random and different configurations. Furthermore, each connector 117 may include an irregular shape. In some embodiments, each first strut 113 may have a configuration similar to the other first struts 113, each second strut 117 may have a configuration similar to the other second struts 117, and each connector 117 may have a configuration similar to the other connectors 117, but each first strut 113 may have a configuration different from each second strut 115.

As can be seen e.g., from FIG. 8, all or some projections of the first plurality of projections 50 and/or all or some projections of the second plurality of projections 55 may extend in (e.g., along) a substantially straight line or in a straight line, i.e., they may not comprise any longitudinal curvature from the point from which they extend from the tubular body 30 to their respective free end 60, 65; i.e., they may extend rectilinearly. They may, however, nevertheless comprise barbs or hooks 71 and or may be pin-shaped. The first plurality of projections 50 may extend from substantially the same axial level (relating to the axial direction of the tubular body 30) from the tubular body 30 (e.g., shown in FIGS. 1 to 3) or may extend from different axial levels from the tubular body 30. Correspondingly, the second plurality of projections 55 may extend from substantially the same axial level (relating to the axial direction of the tubular body 30) from the tubular body 30 (e.g., shown in FIGS. 1 to 3) or may extend from different axial levels from the tubular body 30. The axial extension of the first plurality of projections 50 (axial distance (along axis 35 of tubular body 30) between base of projection on the tubular body and free end of projection) and/or of the second plurality of projections 55 may be substantially the same or may be different, and the extension or length of the first plurality of projections 50 and/or of the second plurality of projections 55 (distance between bases of the projections 50, 55 on the tubular body 30 and the free ends 60, 65 of the projections 50, 55) may be the same or may be different.

In addition to the first and second plurality of projections 50, 55, the tubular body 30 may be provided with any other type of projection and/or collar.

The first 50 and the second 55 pluralities of projections may extend from the first 31 and the second 32 body sections, respectively, from areas that are adjacent to or are bordering the radially outer circumference of the circumferential groove 45. The first 50 and the second 55 pluralities of projections may extend from the opposite side walls 48, 49 laterally defining the groove 45.

Referring to FIG. 2, the free ends 60 of the first 50 plurality of projections may be axially spaced from the free ends 65 of the second 55 plurality of projections by an axial distance W2 in a direction of the axis 35 of the tubular body 30. The free ends 60 of the first plurality of projections 50 may be arranged on a same axial level or on different axial levels, and the free ends 65 of the second plurality of projections 55 may be arranged on a same axial level or on different axial levels.

In case a transcatheter valve prosthesis 1 comprises a plurality of projections 50, 55, the axial distance W2 may define a distance of one or more or all of the free ends 60, 65 of the (one) plurality of projections 50, 55 to a sidewall 48, 49, that is opposite to the respective body section 31, 32 from which the plurality of projections extends, of the circumferential groove 45.

The projections of the first plurality of projections 50 may axially overlap with the projections of the second plurality of projections 55 (not shown), wherein there may be defined an axial overlapping-distance between the free ends 60 of the first plurality of projections 50 and the free ends 65 of the second plurality of projections 55. Some free ends 60 of the first plurality of projections 50 may be axially spaced from corresponding free ends 65 of the second plurality of projections 55, while other free ends 60 and 65 may be arranged so as to axially overlap each other.

Figure 2A:
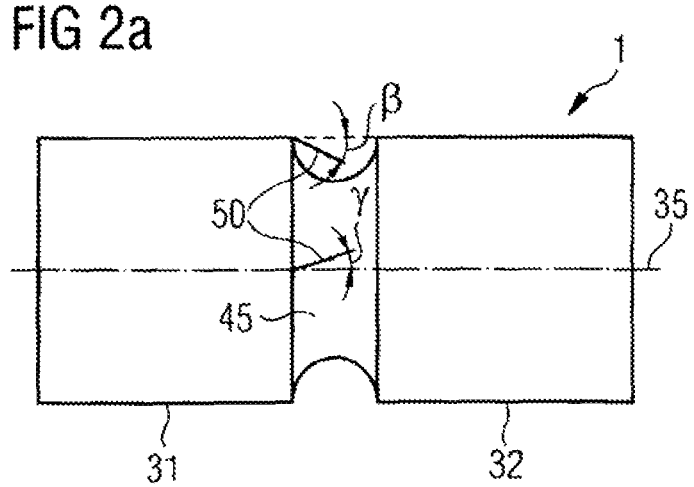

With reference, for example, to FIG. 2a, the projections 50, 55 (each) may extend in a manner so as to be radially and inwardly inclined by an angle $\beta$, thereby obliquely extending into the outer circumferential groove 45. The angle $\beta$ defining the radial and inward inclination of the projections 50, 55 with respect to the axis 35 of the tubular body 30 may be an acute angle, for example in a range of equal to or smaller than 45° or equal to or smaller than 30°, or equal to or smaller than 15°. Only a part or number of the first projections 50 and/or only a part or number of the second projections 55 may radially and inwardly inclined as above described.

FIG. 6a, which corresponds to the cross section along A-A shown in FIG. 3, illustrates the interaction of heart valve tissue of the connection channel wall structure 25 and the first plurality of projections 50 (a cross-section transverse the axis 35 and through the second plurality of projections 55 would result in a similar depiction to that shown in FIG. 6a). The first plurality of projections 50 can be seen perforating tissue of the connection channel wall structure 25 to thereby more reliably prevent it from retracting from the tubular body 30 of the prosthesis 1, which results in the prosthesis 1 being held more firmly in its intended place.

Figure 6B:
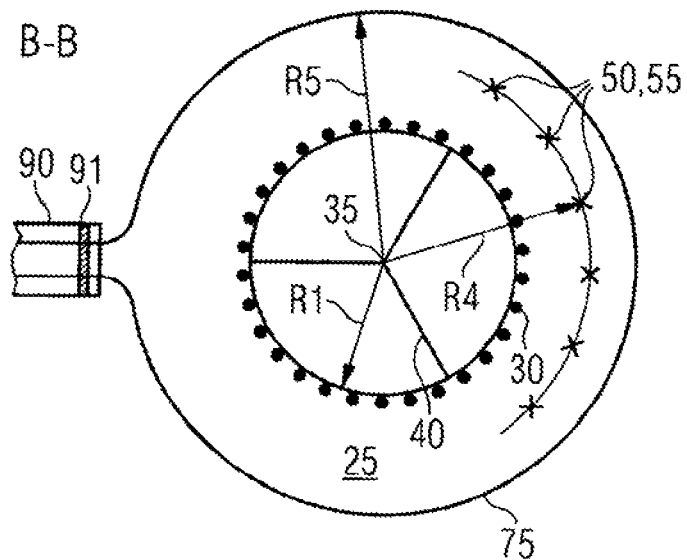
FIG. 6b shows a schematic cross section of a transcatheter valve prosthesis along B-B in FIG. 3.

With further reference to FIG. 3 and FIG. 6b, the transcatheter atrioventricular valve prosthesis 1 may further comprise an elongate outer member 75. The elongate outer member 75 may be disposed at the exterior of the connection channel wall structure 25 (e.g., in the ventricular chamber 20) at an axial level (e.g., with respect to axis 35) of the circumferential groove 45 of the tubular body 30. The elongate outer member 75 may extend at least partially around, for example completely and continuously circumferentially around, the tubular body 30 and may be handled e.g., using a catheter member 90 that is shown schematically in FIG. 6b. A radial distance R5 between the longitudinal axis 35 and the elongate outer member 75 may be reducible or reduced so that the valve tissue of the connection channel wall structure 25 can be correspondingly at least partially forced into the outer circumferential groove 45 so as to be at least partially located radially below the first and second pluralities of projections 50, 55. The radial distance R5 may be reducible or reduced so that it is smaller than a radial distance R4 that is defined between the longitudinal axis 35 of the tubular body 30 and the free ends 60, 65 of the projections 50, 55 (the free ends 60, 65 are not visible in the cross section shown in FIG. 6b, but they are indicated by crosses in FIG. 6b). Thus, the elongate outer member 75 may be positioned inside the circumference defined by the first and second pluralities of projections 50, 55 so that tissue of the connection channel wall structure 25 is or can be located in the circumferential groove 45 between the groove bottom 46 and the first and second projections 50, 55, wherein the elongate outer member 75 itself may be located inside the groove 45 between the groove bottom 46 and the first and second pluralities of projections 50, 55. However, the elongate outer member 75 may also be arranged to force tissue of the connection channel wall structure 25 into the circumferential groove 45 but to remain outside the groove (i.e. R5 may be larger than R4 as shown in FIG. 6b). The catheter member 90, or another, for example similarly structured catheter device, may be used to handle and position the elongate outer member 75 around an exterior of the circumferential connection channel wall structure 25.

With further reference to FIGS. 6b and 7, the catheter member 90 may comprise a connector 91, for example a cutting and clamping member, that can be used to connect free ends of the elongate member 75, for example to cut the elongate outer member 75 and clamp two ends of it together, so that the elongate member 75 may remain permanently around the tubular body 30 and thereby form a component of the prosthesis 1. However, the elongate outer member 75 may also merely be an interventional tool, for example as a component of catheter member, and may only be used to radially force the tissue of the connection channel wall structure 25 into the outer groove 45, and may then be withdrawn or removed from the heart. When the elongate member 75 remains permanently positioned around an outer side of the connection channel wall structure 25, it may permanently apply a radial and inwardly, axially, or outwardly directed force to the tissue of the connection channel wall structure 25 towards the groove 45.

With reference to FIGS. 1, 3, 6b and 7, there may be several ways in which heart tissue of the connection channel wall structure 25 is fixed, held and/or caught in the circumferential groove 45. The tissue may be perforated by the free ends 60, 65 of the first and/or the second plurality of projections 50, 55, e.g., via the acute ends 70 and/or the barbs or hooks 71. The tissue may be held in the circumferential groove 45 by an interference fit between the projections 50, 55. The tissue may also be held in the circumferential groove 45 by the elongate outer member 75. The elongate outer member 75 may be used to force the tissue into the groove 45 either temporarily (e.g., as a method step during a heart treatment) or permanently (for example, if the cutting and clamping member 91 is used to cut elongate outer member 75 and to connect its two ends together permanently while it is extending around the exterior of the connection channel wall structure 25 as shown in FIG. 7). The tissue of the connection channel wall structure 25 may also be held in the circumferential groove 45 by a combination of two or more of the above described approaches.

In embodiments, the elongate outer member 75 may have a cross-sectional diameter D1 (see e.g., FIG. 6b) that is smaller than a width W1 of the outer circumferential groove 45 (illustrated e.g., in FIG. 2). The elongate member 75 may have a cross-sectional diameter D1 that is smaller than the gap W2 between the free ends 60, 65 of the first and the second plurality of projections 50, 55. The elongate member 75 may have a cross-sectional diameter D1 that is larger than width W2 but smaller than width W1. The elongate member 75 may have a cross-sectional diameter D1 that is larger than width W2 and/or width W1. The elongate member 75 may be a wire or a band, and may have a circular cross section or a rectangular cross section. The elongate member 75 may also have a triangular cross section or a cross section defining any other curved or polygonal shape. The elongate member 75 may be made from any material that has been described with reference to the mesh elements 33 or a combination of those materials or other material(s). For example, the elongate member may be made from steel, a titanium alloy or a shape memory alloy such as nitinol.

A length of the projections 50 and/or 55 may be related to the width W1 of the circumferential groove 45. In this respect, the ratio of a distance between the free ends 60, 65 of the first and second pluralities of projections 50, 55 (or, if only one plurality of projections 50, 55 is provided, a distance of the free ends 60, 65 of that plurality of projections 50, 55 to the sidewall 48, 49 of the circumferential groove 45 that is with respect to axis 35 opposite to the projections 50, 55) to the width W1 of the circumferential groove 45 may have a maximum value of 0.5 or 0.4 or 0.3 or 0.2 or 0.1. Accordingly the hollow chamber 66 may be defined between the projections 50, 55 and the groove bottom 46. The width W1 of the circumferential groove 45 may be defined between the sidewalls 48, 49 of the groove 45 and or between a point from which a projection 50, 55 of the first and/or second plurality of projections 50, 55 extends from the tubular body 30 and a sidewall 48, 49 that is located on an opposite side of the groove (45) and/or between a point from which a projection from the first plurality of projections 50 extends and a point from which a projection form the second plurality of projections 55 extends.

Figure 5:
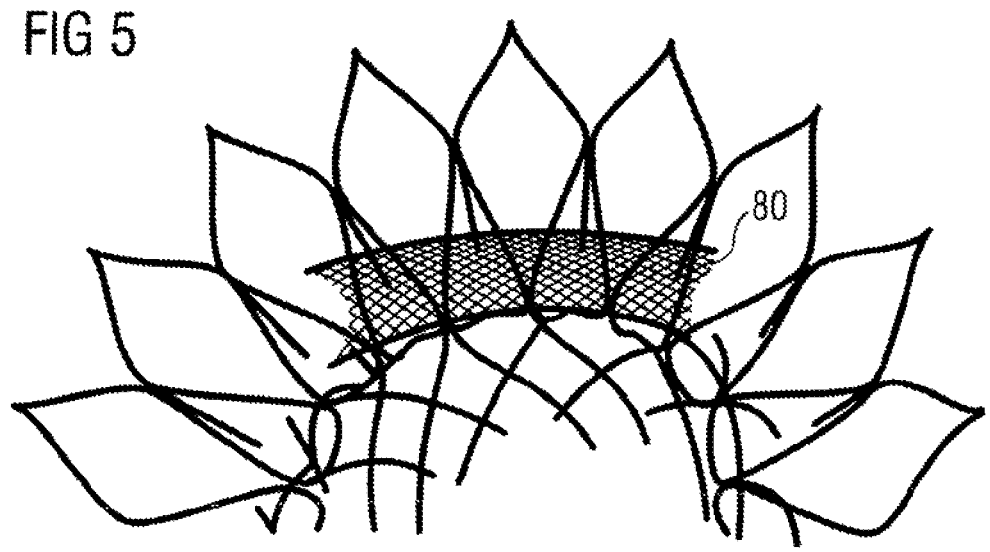
FIG. 5 shows the transcatheter valve prosthesis including the clamping member of FIG. 4 from a different perspective.

With reference to FIGS. 4 and 5 (for improved clarity and understanding, the transcatheter valve prosthesis 1 is shown without artificial valve 40), the transcatheter valve prosthesis 1 may also comprise a clamping member 80. The clamping member 80 may comprise a tubular structure having a longitudinal axis that may be arranged so as to extend in the circumferential groove 45 in a circumferential direction of the tubular body 30. The clamping member 80 may be located in the circumferential groove 45 so as to be located (for example at least partly) radially inwards of the first and second pluralities 50, 55 of projections. The clamping member 80 may be in contact with the groove bottom 46 of the circumferential groove 45. The clamping member 80 may extend around a whole circumference of the tubular body 30 or only partially around the tubular body 30, as shown, e.g., in FIGS. 4 and 5. The clamping member 80 may extend, e.g., around an angle of 10 to 30 degrees or any other angle in the circumferential groove 45. The clamping member 80 may extend around the whole circumference of groove 45, e.g., around 360 degrees. The clamping member 80 may have a cross-sectional diameter D2 transverse to its longitudinal axis. The cross-sectional diameter D2 may be selectively changeable to a larger or smaller diameter D2; i.e., the clamping member 80 may be compressible (so as to be insertable via a catheter) and/or expandable (for example, re-expandable after being compressed) in a radial direction of its diameter D2, whereby the inner and outer circumferences of the clamping member are correspondingly decreased/expanded and expanded/decreased, respectively, in a radial direction of the tubular body 30 towards the first and/or the second plurality of projections 50, 55. The cross sectional diameter D2 of the clamping member 80 may be smaller than the cross sectional diameter (radius R1 is shown, e.g., in FIG. 6a) of the tubular body 30. In embodiments, the diameter D2 of the clamping member 80 may be smaller than the width W1 of the outer circumferential groove 45 and smaller than the width W2 of the gap formed between the free ends 60, 65 of the first and the second plurality of projections 50, 55. The clamping member 80 may be provided in order to clamp heart tissue that is located inside the circumferential groove 45 outwards in a direction from the axis 35 towards the pluralities of projections 50, 55.

The clamping member 80 may include a delivery configuration within a delivery catheter and a deployment configuration wherein the clamping member 80 is deployed from the delivery catheter. In embodiments, the clamping member 80 may be biased to the deployment configuration. For example, the clamping member 80 may include a shape-memory alloy such as a nitinol or a nitinol-based alloy that has a delivery configuration that is shaped to be convenient for delivery through a catheter, and a deployment configuration in which the shape-memory alloy changes shape to a deployed configuration so as to be biased to a shape conforming to the tubular body.

With reference to FIG. 6d, the clamping member 80 may be or form part of the above-described elongate outer member 75, wherein the clamping member 80 may be arranged and or guided and/or positioned (in a radially compressed condition) at the circumferential outer side of the connection channel wall structure 25 to completely or partly extend around the connection channel wall structure 25 at an axial (with respect to the axis 35 of the tubular body 30) level, and may then be radially expanded (in a direction of the diameter D2 of the clamping member 80), whereby its inner diameter in a radial direction of the tubular member 30 then correspondingly decreases to thereby force the tissue of the inwardly arranged connection channel wall structure 25 (which is then arranged inwards of the clamping member 80) radially into the groove 45. That is, the clamping member may be located between the projections 50, 55 and tissue of the connection channel wall structure 25, that may be pressed into the groove 45 by an elastic force exerted by the clamping member 80 on the tissue of the connection channel wall structure 25 and a corresponding reactive force that may be exerted by the clamping member 80 on the projections 50, 55. The forces that may act upon the tissue of the connection channel wall structure 25 exerted by the clamping member 80 and the groove 45 (e.g., the groove bottom 46) are schematically indicated by arrows 85b. The elongate outer member 75 and/or the clamping member 80 (which may be the same member) may serve to anchor the prosthesis 1 and to seal the native heart leaflets against the prosthesis 1 against blood flow. Further, immobilization of the native leaflets by the prosthesis 1 as described herein (e.g., comprising a clamping member 80 and/or elongate member 75) may favor the ingrowth of heart (e.g., leaflet) tissue into the prosthesis (e.g., circumferential groove 45) and thereby further improve fixation of the prosthesis 1 relative to the heart and/or sealing against blood flow as the ingrown tissue may additionally or alternatively seal against blood flow on an outside of the tubular body 30.

Figure 20:
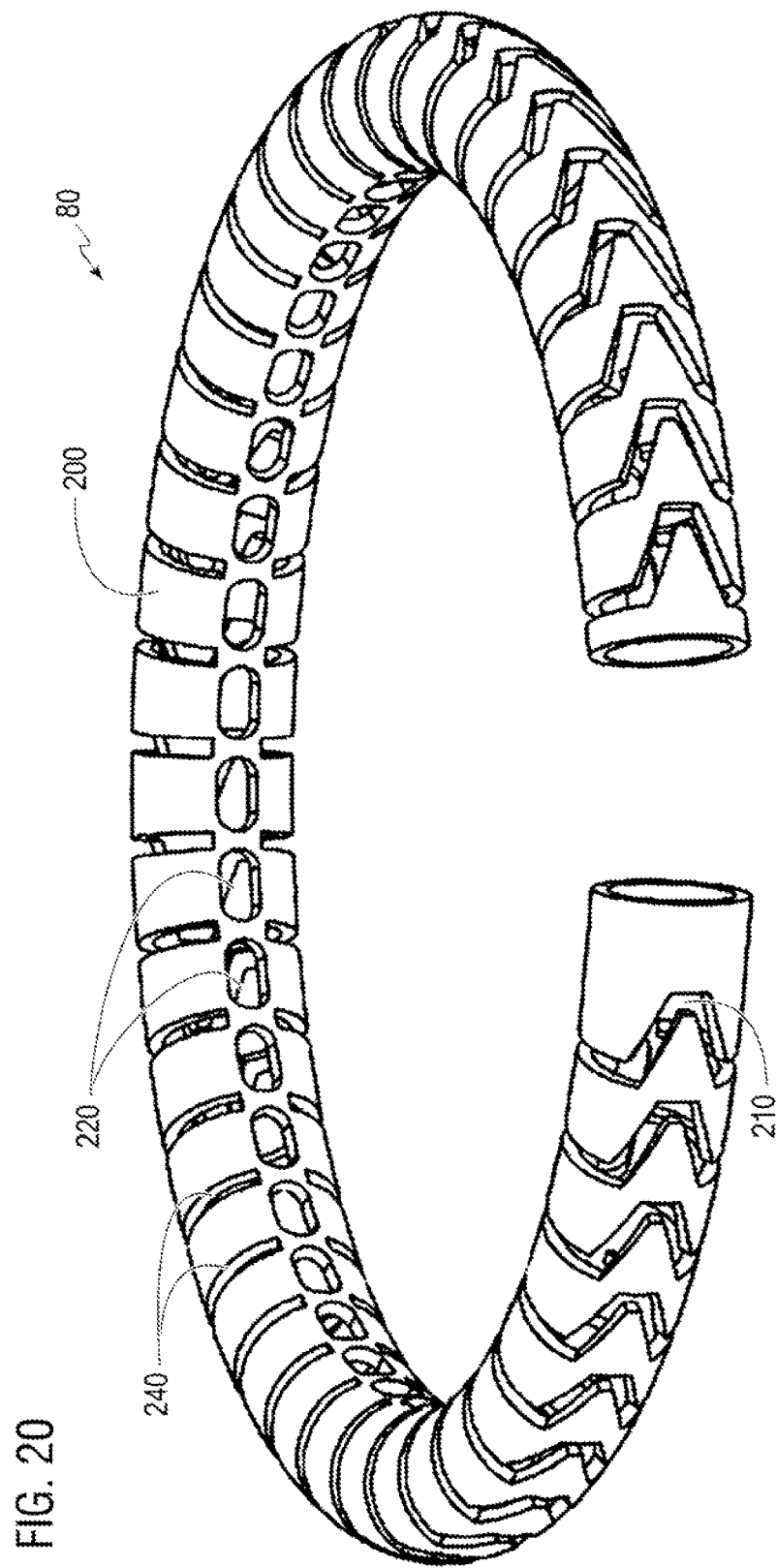

In some embodiments, the clamping member 80 may include one or more barbs 230 configured to secure the prosthesis 1 to portions of the native valve leaflets and/or chords when the barbs 230 are deployed, for example, by piercing the portions of native valve leaflets and/or barbs. For example, as shown in FIG. 20, the clamping member 80 may include an inner member 210 slideably disposed within a hollow outer tube 200. It is further contemplated that the outer tube 200 may be slideably disposed with regard to the inner member 210. One or more flexible regions 240 may be disposed on the outer tube 200 to facilitate bending of the clamping member 80. The flexible regions 240 may include cutouts, for example as shown in FIG. 20, or may include material sufficient to facilitate such bending of the clamping member 80. The cutouts may be of various shape and sizes. Additionally, the flexible regions 240 may be disposed consistently or intermittently on outer tube 200.

Figure 22:
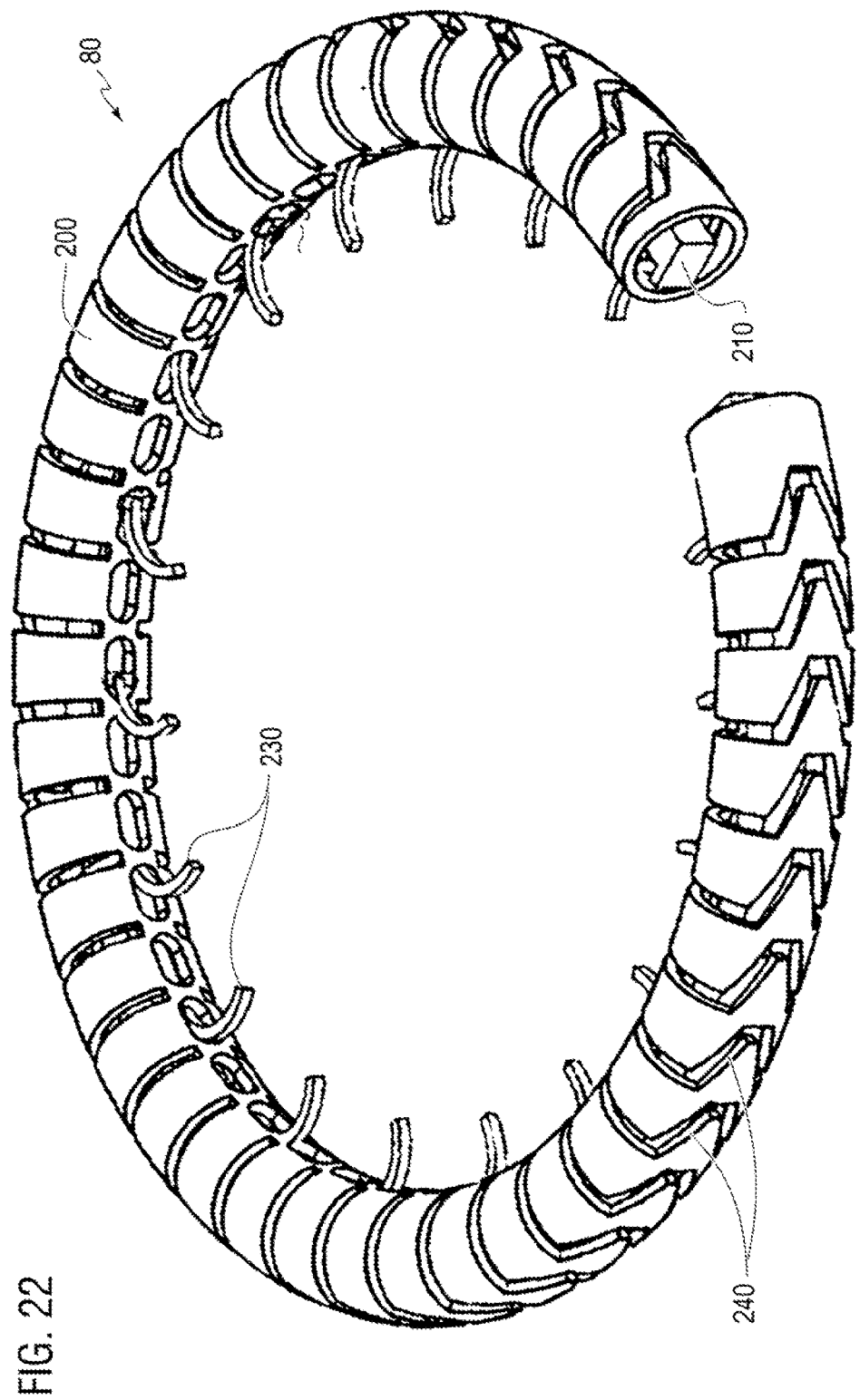

One or more openings 220 may be disposed through an outer surface of the outer tube 200, such that the openings 220 are coupled with one ore barbs 230 on the inner member 210. For example, the barbs 230 may each be configured to assume a first delivery configuration wherein the barbs 230 are disposed substantially parallel to the inner member 210 and are disposed within the outer tube 200. For example, the barbs 230 may lay substantially flat along the inner member 210. Movement of the inner member 210 relative to the outer tube 200 may substantially align the barbs 230 with the openings 220 such that the barbs 230 move from the first delivery configuration to a second deployment configuration. For example, as shown in FIG. 22, the barbs 230 may extend away from the clamping member 80, and may be configured to attach to the native leaflets and/or chords. Therefore, the barbs 230 may be deployed through the openings 220 when in the deployment configuration.

Various means may be used to deploy the barbs 230 from their delivery configuration to their deployment configuration. For example, the barbs 230 may be comprised of a superelastic material such that they immediately assume the deployment configuration once aligned with openings 220. In other embodiments, the barbs 230 may be moved into the deployment configuration through a hydraulic force (for example, by the inflation of a balloon), pushing of the barbs 230, rotating of the barbs 230, a spring mechanism, and/or thermal electric current.

The barbs 230 may be deployed, and assume the deployment configuration, before the tubular body 30 is fully deployed. For example, the barbs 230 may be deployed when the tubular body 30 is partially deployed. Alternatively, the barbs 230 may be deployed after the tubular body 30 is fully deployed.

Figure 21:
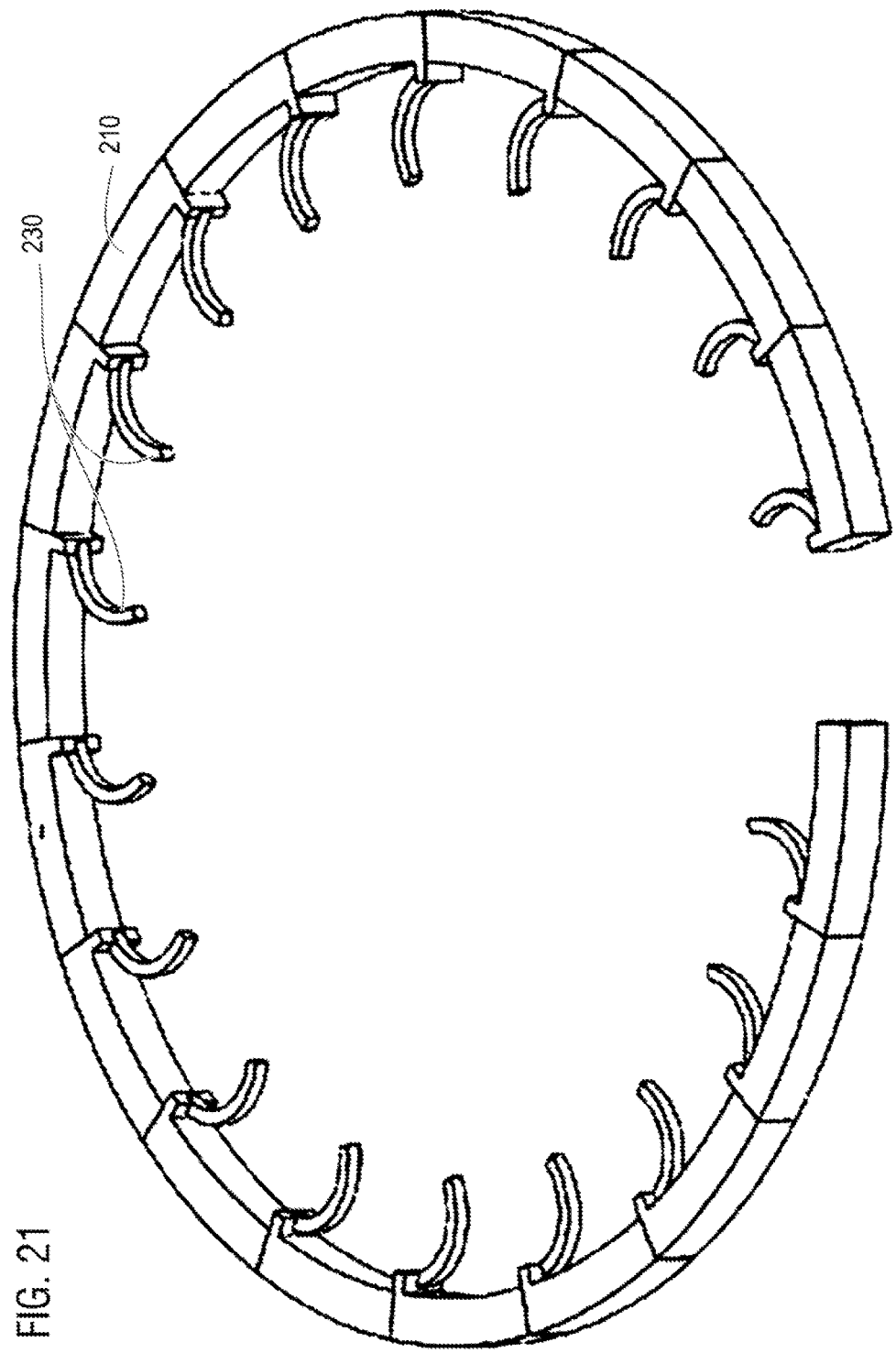
Figure 23:
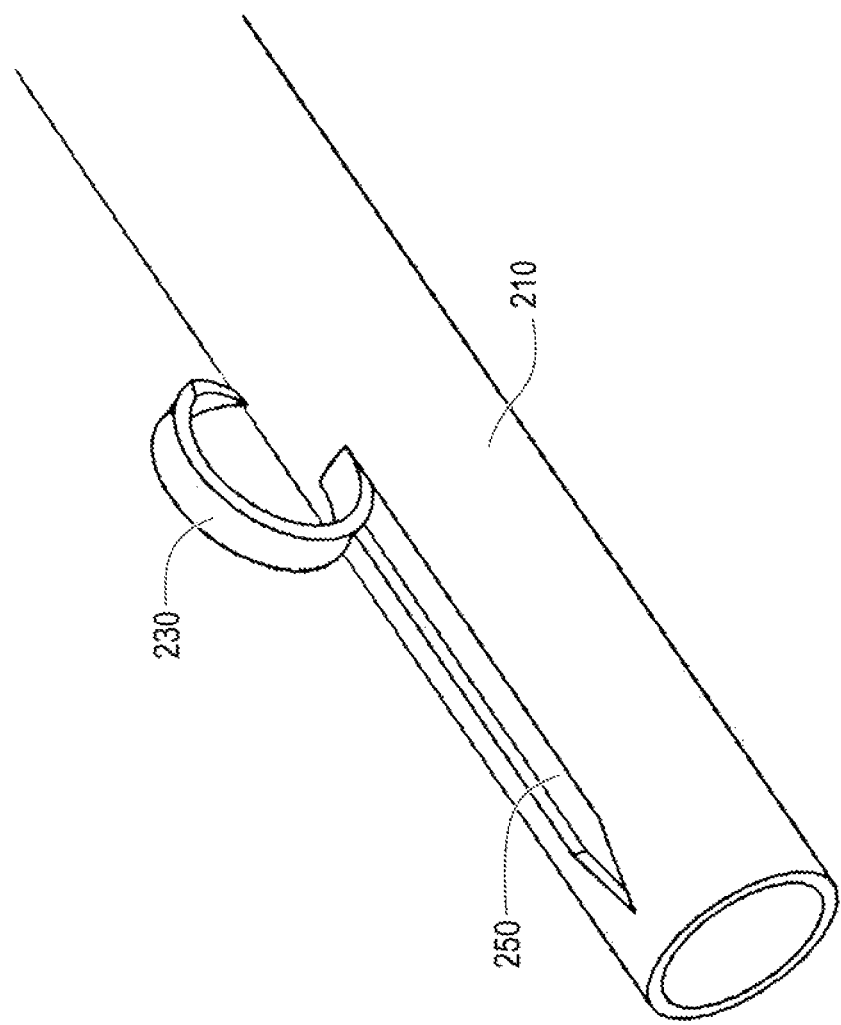
Figure 24:
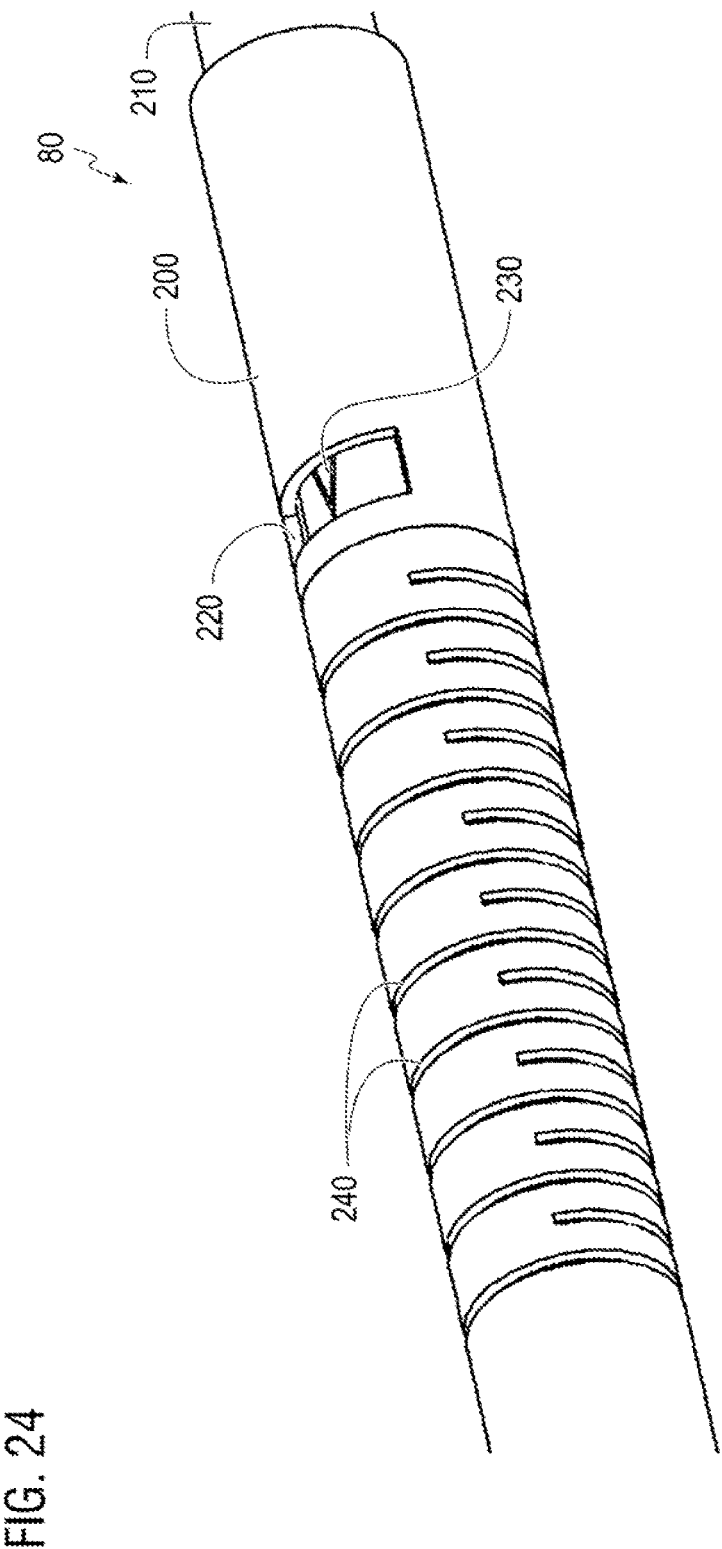
Figure 27:
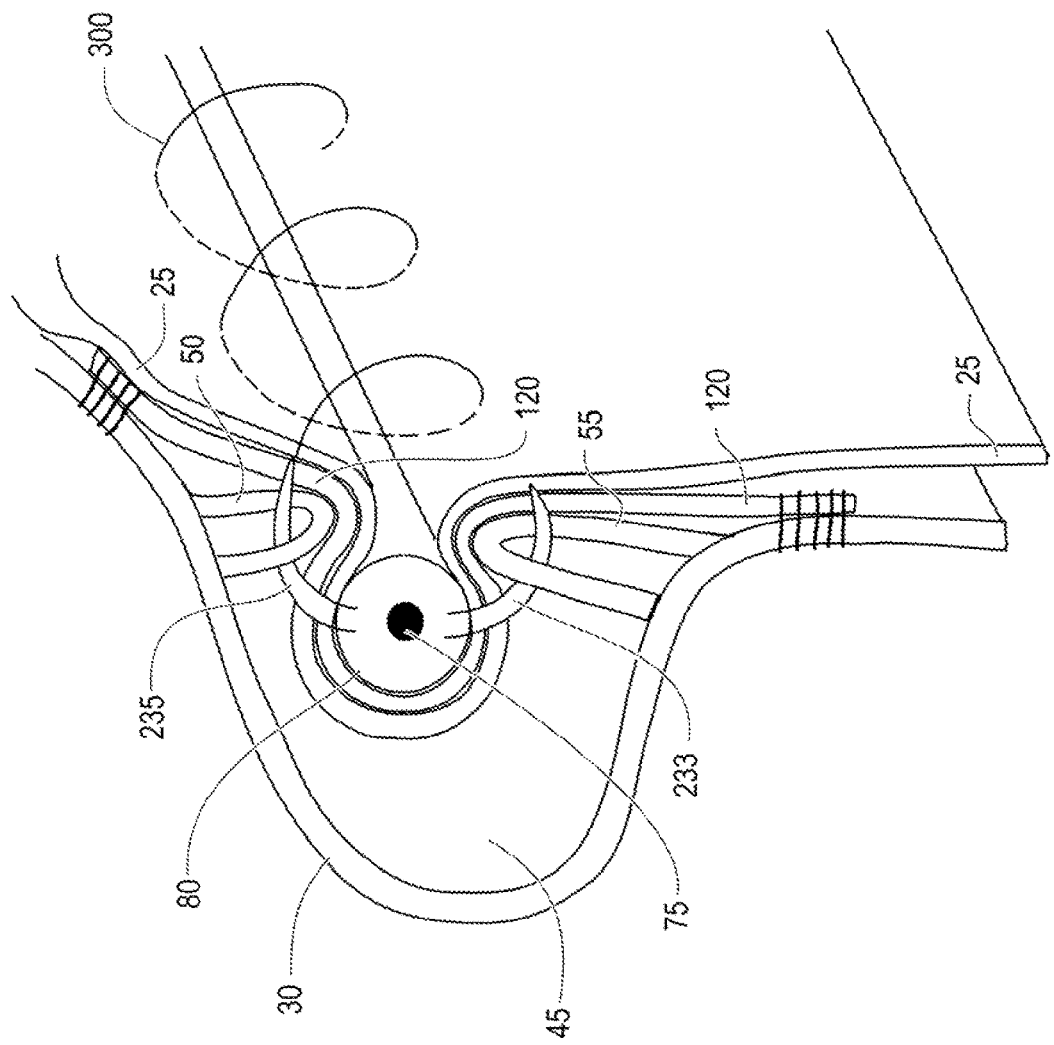

The delivery configuration of the barbs 230 may be substantially perpendicular to the deployment configuration of the barbs 230. Additionally, the barbs 230 may be arcuate when in the deployment configuration, for example as shown in FIGS. 21 and 23. It is further contemplated that the barbs 230 may constitute a helical structure configured to be driven into the connection channel wall structure 25 when the barb is rotated about its longitudinal axis (FIG. 27). The helical structure may pierce adjacent native leaflets and/or chords (e.g. a first portion and a second portion) to secure the adjacent native leaflets and/or chords together, as shown in FIG. 27. The helical structure may include a helical needle. In some embodiments, a suture may be advanced from the helical needle to secure the adjacent native leaflets and/or chords together.

Figure 26:
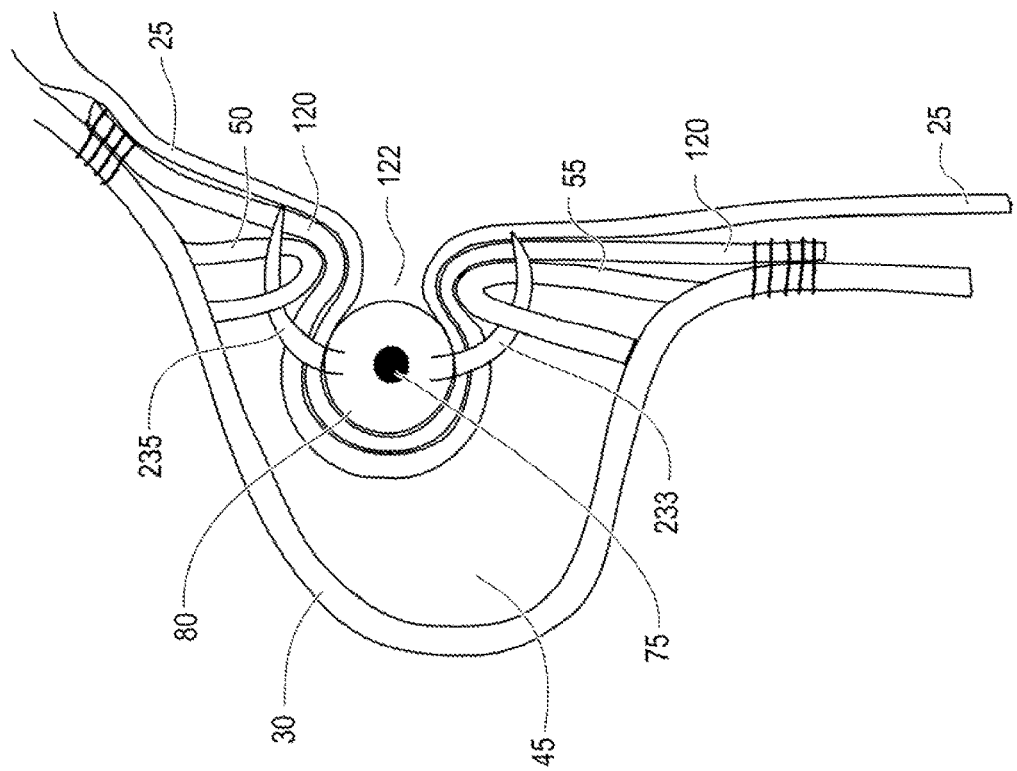

In some embodiments, the clamping member 80 may include a first set of barbs 233 configured to be oriented toward an inflow side of the circumferential groove 45 when the clamping member 80 at least partially encircles the circumferential groove 45, as shown in FIG. 26. Additionally or alternatively, the clamping member 80 may include a second set of barbs 235 configured to be oriented toward an outflow side of the circumferential groove 45 when the clamping member 80 at least partially encircles the circumferential groove 45.

The inner member 210 may include one or more slits 250 on an outer surface of the inner member 210. Each barb 230 may be disposed within a slit 250 when the barb 230 is in the delivery configuration. Therefore, the inner member 210 may be configured to slide within the outer tube 200 without interference from the barbs 230. Additionally or alternatively, the inner member 210 and/or the outer tube 200 may be coated with a lubricious coating to facilitate the sliding of the inner member 210 relative to the outer tube 200.

Figure 25A:
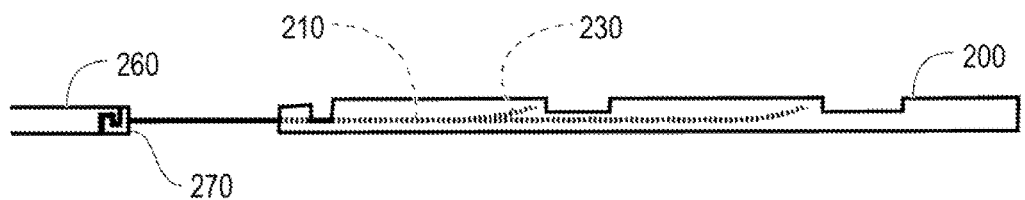
Figure 25B:
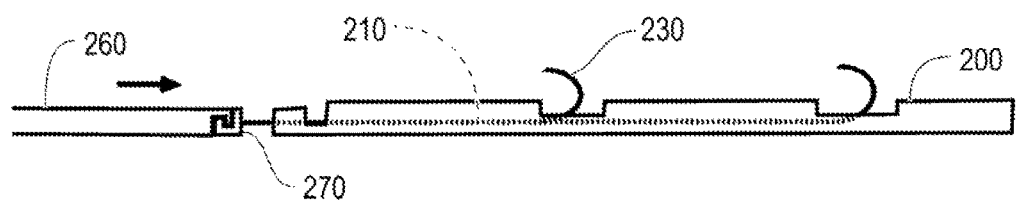
Figure 25C:
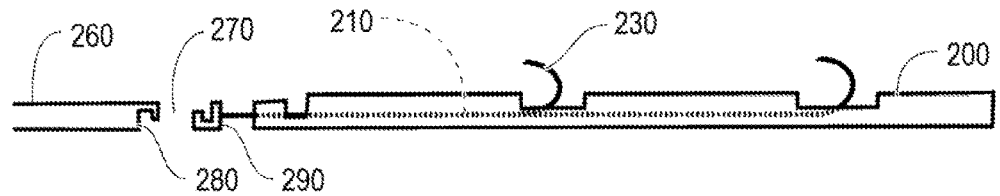

A pusher tube 260 may be configured to push and/or pull the inner member 210 in a longitudinal direction of or rotationally relative to the outer tube 200 to deploy the barbs 230. It is also contemplated that the pusher tube 260 may be configured to push and/or pull the outer tube 200 in a longitudinal direction of or rotationally to the inner member 210 to deploy the barbs 230. As shown in FIGS. 25a-25c, for example, the pusher tube 230 may be releasably attached to the inner member 210 through connection 270. In some embodiments, the connection 270 may include a first connection link 280 on the pusher tube 260 that is releasably coupled to a second connection link 290 on the pusher tube 260. Therefore, the pusher tube 260 may selectively push and/or pull the clamping member 80 when the first connection link 280 is attached to the second connection link 290 to align the barbs 230 with openings 200 to deploy the barbs 230. Additionally, the pusher tube 260 may be selectively released from the inner member 210. In some embodiments, the pusher tube 260 may be advanced over the elongate outer member 75 to deploy the barbs 230. For example, the pusher tube 260 may be connected to inner member 210 through connection 270 and advanced over the elongate outer member 75 with the clamping member 80.

The barbs 230 may be configured to attach to the projections 50 and/or 55 to secure the prosthesis 1 to the portions of native valve leaflets and/or chords. For example, as shown in FIGS. 26 and 27, the first set of barbs 233 may be disposed through projections 55 and the second set of barbs 235 may be disposed through projections 50. As shown in FIGS. 26 and 27, the shape of the barbs 230 secures the barbs 230 to the projections 50, 55. It is further contemplated that other well-known attachment means may be used to secure the barbs 230 to the projections 50, 50, for example, including but not limited to, sutures, adhesive, clamps, etc.

The circumferential opening of the groove 45 may be defined by an indent in a side surface of the tubular body 30, and the groove 45 may be larger than a maximum outer diameter of the clamping member 80, as shown in FIGS. 26 and 27. Therefore, the attachment of the barbs 230 to the portions of native valve leaflets and/or chords may secure the prosthesis 1 to the portions of native valve leaflets and/or chords. Withdrawal of the barbs 230 away from and out of the portions of native leaflets and/or chords may thus cause the prosthesis 1 to no longer be secured to the portions of native valve leaflets and/or chords.

In embodiments, when partially deployed, such that the outflow end but not the inflow end is deployed from a delivery catheter, the tubular body 30 may form a frustoconical shape that slopes radially outward from the circumferential groove 45 and toward the outflow end. For example, the tubular body 30 may slope radially outward approximately 2°-45° with regard to a longitudinal center axis of the tubular body 30 when partially deployed. In embodiments, the tubular body 30 may slope approximately 5°-30°, or approximately 10°-20°, or approximately 15° with regard to the longitudinal center axis of the tubular body.

In the partially deployed state, the elongate outer member 75 maybe slid along the tubular body 30 to guide tissue of wall structure 25 (e.g., native valve leaflets and/or chords) into the circumferential groove 45. For example, the elongate outer member 75 may slide in a direction moving radially inward along the slope of the tubular body 30 from an outflow end of the tubular body toward an inflow end of the tubular body 30 and into circumferential groove 45. When sliding along the frustoconical shape of the partially deployed tubular body 30, the elongate outer member 75 may be disposed outside the wall structure 25 and therefore slide along the tubular body 30 and along the wall structure 25. Therefore, elongate outer member 75 may move the native valve leaflets and/or chords of the wall structure 25 into the circumferential groove 45 such that the native valve leaflets and/or chords are disposed between the tubular body 30 and elongate outer member 75 (FIG. 10c). This may trap the native valve leaflets and/or chords within the circumferential groove 45.

FIG. 6c shows a schematic cross sectional view of the tubular body 30 and the clamping member 80 similar to the cross section C-C in FIG. 4, however additionally showing heart tissue of the connection channel wall structure 25 that is not shown in FIG. 4. In FIG. 6c, the positions of the first or second pluralities of projections 50, 55 are indicated by dots 50, 55. As can be seen from FIG. 6c, the heart tissue of the connection channel wall structure 25 is located inside the circumferential groove 45 radially between the groove bottom 46 of the tubular body 30 and a diameter that is defined by the free ends 60, 65 of the first and/or the second plurality of projections 50, 55. It can be seen from FIG. 6c that the clamping member 80 is elastically strained by the tissue of the connection channel wall structure 25 and in turn exerts a force that presses the tissue of the connection channel wall structure 25 against the free ends 60, 65. Arrows 85 indicate the forces that are caused by the clamping member 80 and that act upon the tissue of the connection channel wall structure 25 in the groove 45.

With reference, e.g., to FIGS. 6c and 6d, which show only one clamping member 80, there may also, e.g., be two or more clamping members 80 arranged in the groove 45 which are arranged in parallel to each other and/or which are arranged sequentially in a circumferential direction, with for example a circumferential distance therebetween or abutting each other, of the tubular body 30. For example, there may be two clamping members 80 abutting each other and a third clamping member 80 that has an angular distance from the two clamping members 80 that are abutting each other may also be arranged in the groove 45. Clamping members 80 may, e.g., be positioned on diametrically opposite sides of the groove 45. These two or more (e.g., 3 to 5) clamping members 80 may all have the same cross-sectional diameter D2 or may each have different cross-sectional diameters. The clamping members 80 may all have the same longitudinal length or may have different longitudinal lengths (e.g., in a circumferential direction of tubular body 30). Clamping members 80 may be designed and arranged so that the tubular body 30 is firmly held in place according to the specific tissue structure and conditions of the connection channel wall structure 25 of a specific heart (e.g., of a patient). They may, e.g., be specifically chosen and arranged by an operator or surgeon to firmly hold the tubular body 30 in place according to local conditions. The respective clamping member 80 may have a shape other than a tubular shape, such as a block-shape, a cubic-shape or a ball-shape.

The force acting on the tissue of the connection channel wall structure 25 may be increased when the clamping member 80 is used together with the elongate outer member 75, thereby further improving the connection between the transcatheter valve prosthesis 1 and the connection channel wall structure 25. In this case, an elastic force originating from the clamping member 80 pointing from the axis 35 outwards, and a force originating from the elongate outer member 75 pointing inwards to the axis 35, act upon tissue of the connection channel wall structure 25, thereby holding the prosthesis 1 firmly in its intended position in the connection channel 10. However, the valve prosthesis 1 may be used without the clamping member 80 and the elongate outer member 75 as well (i.e., by itself), or together with only one (any one) of them. A prosthesis 1 not comprising a plurality of projections 50, 55 may be fixed by clamping member 80 and/or elongate outer member 75, e.g., when the elongate outer member 75 and/or the clamping member 80 are/is generally rigid, e.g., when comprising or being an inflatable balloon that is filled with a substance giving it rigidity caused by a pressure or by a curing of that substance. If present, that substance can cure within a limited amount of time, with the injection of an additional agent (e.g., a reticulating agent), with application of heat or energy. It can be, for example, PMMA (Poly Methyl Methacrylate), different epoxies, polyurethane, or a blend of polyurethane silicone. It can be strengthened, for example with the addition of reinforcement fibers (e.g., polyaramid such as Kevlar®, carbon).

Clamping member 80 may be made from a mesh-type structure as shown in FIGS. 4 and 5 and may comprise an inner lumen. The mesh may be made from metal or organic material or other material. The mesh of clamping member 80 may be made, e.g., from iron, nickel, aluminum and/or titanium and/or alloys of these metals and other elements. The mesh may be made, e.g., from steel (e.g., spring steel), and/or a superalloy and/or shape memory alloy (such as, e.g., nitinol), $Ti_6Al_4V$, and/or a precious metal like gold, or any combination of those and/or other materials. The mesh of clamping member 80 may also be made from polymers, e.g., from polypropylene or polyvinylchloride, polyethylene or nylon. Of course, the mesh may also be made from combinations of these materials, i.e., it may be made from two or more different materials. In embodiments, the clamping member can be an expandable stent-graft made with a steel or nitinol stent covered with a polyester or PTE (polyethylene terephthalate) graft material, such as Dacron®, or an ePTFE (expanded Poly Tetra Fluoro Ethylene) graft material. The mesh of clamping member 80 may also or additionally comprise any material that has been described with reference to the mesh elements 33 of the tubular body 30 and/or with reference to the elongate member 75, and the clamping member 80 may be designed and a material for it may be chosen so as to create a high elastic force to press the tissue of the connection channel wall structure 25 against the projections 50, 55. Clamping member 80 may be provided with hooks or barbs to create an attachment to tubular body 30.

Clamping member 80 and/or elongate outer member 75 may comprise an inflatable inner member (not shown). The inflatable inner member may be disposed in an inner lumen of the clamping member 80 and may be inflated so as to increase diameter D2 of clamping member 80, thereby pressing tissue of the connection channel wall structure 25 against the projections 50, 55 (either from an inner side if the clamping member 80 is arranged in the hollow chamber 66 or from an outer side if the clamping member 80 is arranged at an outer side of the connection channel wall structure 25). The inner member may be inflated by the operator using a tubing and fluid (gas or liquid) from an external pressure source, e.g., a syringe, a fluid bottle or a pump located outside the body. The clamping member 80 may be an inflatable member 80 that presses tissue of the connection channel wall structure 25 against the projections 55, 55 when inflated. Both the inflatable inner member and the inflatable member 80 may be made from a fluid tight, pressure resistant material, e.g., a material or polymer as described above with reference to the clamping member 80, or any other suitable material. With reference to, e.g., 11a-11b, the inflatable member may comprise an aperture 76 (e.g., a valve, e.g., an opening) through which a substance (e.g., via a delivery tube (not shown)) may be delivered into the inflatable member and/or out of the inflatable member. The aperture 76 may selectively permit the transmission of a substance (i.e., have an "open-state") or may block the transmission of a substance (i.e., have a "closed-state"). The aperture 76 may serve to fill the inflatable member or to un-fill (e.g., to empty) the inflatable member in order to change a cross-sectional diameter of the inflatable member. The clamping member 80 and/or the elongate outer member 75 may be made of an elastic material (e.g., a polymer and/or a metal) and/or may be filled with a compressible (e.g., elastic) substance (e.g., a gas and/or a foam material and/or a hydrogel) to provide a damping/cushioning functionality. A substance for filling the inflatable member may be a gas, a liquid or any other substance and/or may be a substance that changes its phase (e.g., gas, liquid, solid) when in the inflatable member (the substance may, e.g., change from liquid phase to a generally solid phase). The substance may be a substance that is capable of curing and/or hardening when disposed in the inflatable member so as to provide a generally rigid clamping member 80 and/or elongate outer member 75.

Clamping member 80 may apply a force to the opposite side walls 48, 49 of groove 45, for instance upon radial expansion relative to its longitudinal axis. This force may increase or decrease the distance between body sections 31 and 32 and/or the distance between axial ends (with respect to axis 35) of the tubular body 30. Tubular body 30 may be made to be elastic (e.g., comprising a mesh structure and/or an elastic material). The force exerted by clamping member 80 may result in an expansion or reduction of a perimeter of the groove bottom 46 along a circumference of groove 45 and/or in an expansion or reduction of diameter R1 of the tubular body 30 at an axial height (with respect to axis 35) of groove 45 respectively. The clamping member 80 and/or the elongate outer member 75 (which may be the same member or may be separate members) may also not produce a force in a radial direction and/or a longitudinal direction of the tubular body 30 with respect to its longitudinal axis 35. Accordingly, the clamping member 80 and/or the elongate outer member 75 may act as a displacement member by displacing tissue of the connection channel 10 without exerting a clamping force to the tubular body 30 but by providing a mere interference fit between the circumferential wall structure 25 of the connection channel 10, the clamping member 80 and/or the tubular body 30 in addition or as an alternative to, e.g., tissue being pierced by projections of the first 50 and/or second plurality of projections 55.

The clamping member 80 and/or elongate outer member 75 may be located only partially radially inwards of the first 50 and/or second 55 plurality of projections and may be located so as to be pierced by any one or both pluralities of projections 50 so as to be held relative to the tubular body 30. The elongate outer member 75 and/or clamping member 80 may be pierced by only one plurality of projections 50, 55 and the other plurality of projections may not pierce the clamping member 80/elongate outer member 75 (or, the other plurality of projections may not be provided in case of a prosthesis 1 only comprising one plurality of projections (on one side of the groove 45)). The plurality of projections 50 and/or 55 may pierce the clamping member 80 so that the respective free ends 60, 65 of the projections 50, 55 end inside the clamping member 80 or so that the free ends 60, 65 of the respective projections 50, 55 penetrate through the clamping member 80 and exit from the clamping member so that the respective free ends 60, 65 may be located outside the clamping member 80.

Figure 10A:
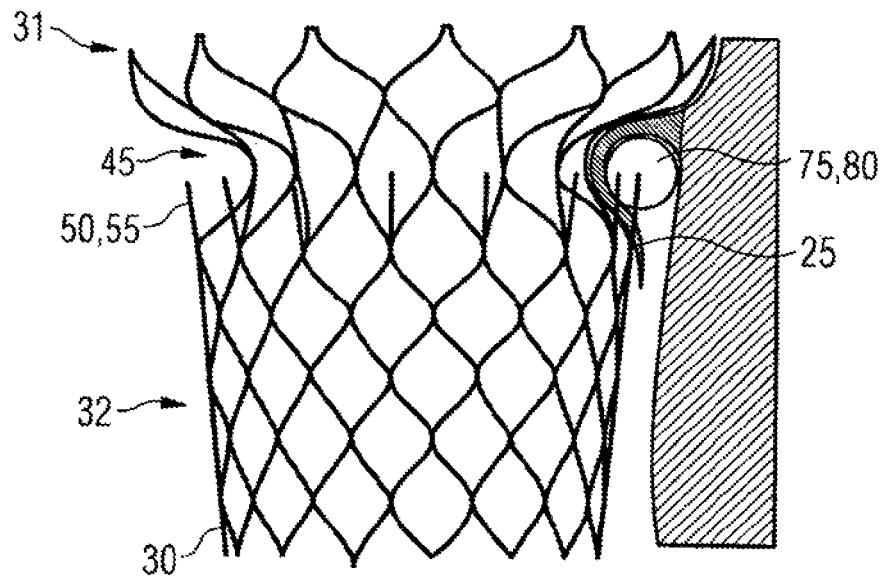
Figure 10B:
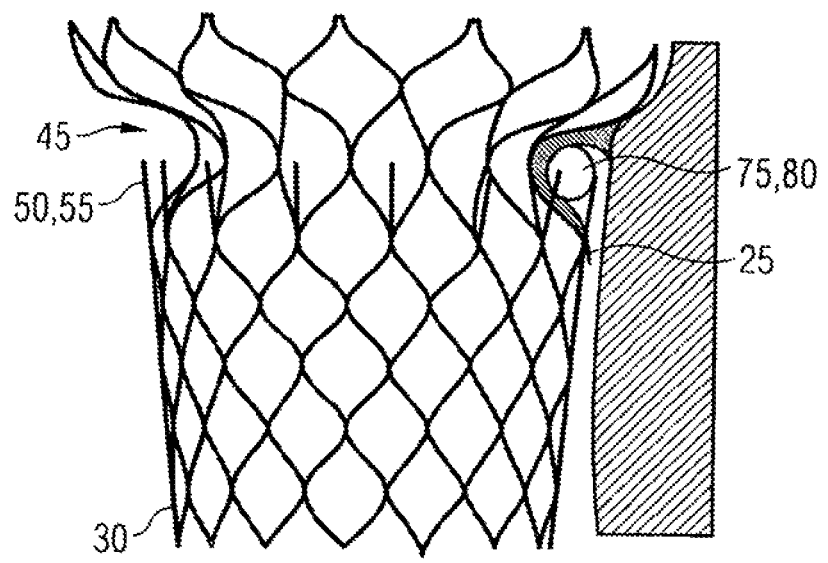

With reference to FIG. 10b, the elongate outer member 75 and/or the clamping member 80 may be provided in the groove 45 radially inwards of the projections 50, 55 so that the elongate outer member 75 and/or the clamping member 80 is not pierced by the projections 50, 55. In embodiments, the clamping member 80 may trap at least portions of native valve leaflets and/or chords within the circumferential groove 45 defined by the tubular body 30 and the first plurality of projections 50 and/or the second plurality of projections 55. For example, the native valve leaflets and/or chords may be disposed between the clamping member 80 and the second plurality of projections 55 within circumferential groove 45. The elongate outer member 75/clamping member 80 may be held by a mere interference fit or a frictional/interference fit between the groove 45, the tissue of the connection channel wall structure 25 and or projections 50, 55 in the groove 45 (e.g., when inflated, e.g., when expanded). Further, as schematically shown in FIG. 10b, the elongate outer member 75/clamping member 80 may have a cross sectional shape that is substantially elliptical or has any other shape, such as a triangular, rectangular or polygonal shape. The substantially elliptical shape of the elongate outer member 75/clamping member 80 that is shown in FIG. 10b may be caused by the design of the elongate outer member 75/clamping member 80, e.g., when it is provided with a tubular structure having a substantially elliptical shape (e.g., when expanded), or it may be caused by anisotropic forces acting upon elongate outer member 75/clamping member 80 caused, e.g., by the projections 50, 55, the tissue of the circumferential wall structure 25 and/or groove 45. That is, the elongate outer member 75/clamping member 80 may have a substantially round cross section when no external forces act upon it and may assume a different shape (e.g., elliptical), when implanted (and, e.g., expanded).

With reference to, e.g., FIG. 10c, an expandable and or reducible elongate outer member 75 (e.g., clamping member 80) may have a diameter D2 that may be larger than width W1 of circumferential groove 45 when expanded so that the elongate outer member 75 may extend out of the groove 45 and may occupy a space between the circumferential wall structure 25 and tissue forming a heart chamber (e.g., the ventricular chamber 20 and/or atrial chamber 15), i.e., the elongate outer member 75 may form a shape arranged between (e.g., abutting) the connection channel wall structure 25 and tissue/muscles of a heart chamber wall (e.g., of ventricular chamber 20) when expanded (e.g., fully expanded). Accordingly, the elongate outer member 75 may be located (e.g., partially, e.g., a part thereof) radially outside (with respect to axis 35) the circumferential groove 45 and may extend parallel to axis 35 along one or both body sections 31, 32 (e.g., along second body section 32) of tubular body 30 while being (e.g., partially, e.g., a part of elongate outer member 75) located radially outside groove 45. Accordingly, the elongate member 75 may comprise an angularly shaped (e.g., substantially describing an angle of about 90°) cross section with a first angular leg 75a that may extend with respect to axis 35 generally radially into the groove 45, and a second angular leg 75b mat may extend generally parallel to axis 35 of the tubular body 30 on an outside of the tubular body 30 (e.g., along first body section 31 and/or second body section 32). That is, the elongate outer member 75 (e.g., second angular leg 75b thereof) may be disposed between the first 31 and/or second 32 body section and tissue/muscle forming a wall of a heart chamber such as the ventricular chamber 20 and/or atrial chamber 15. While in FIG. 10a-c the elongate outer member 75/clamping member 80 is only shown on one side of the prosthesis 1, it may also extend fully or partially (as shown, e.g., in FIG. 11a-d) around the prosthesis 1 (e.g., the circumferential groove 45). The elongate outer member 75/clamping member 80 may comprise free ends 77, 78 (e.g., two free ends 77, 78) in a direction of a central-longitudinal axis that may be non-connected and/or not abutting each other, i.e., spaced away from each other. The free ends 77, 78 may have an angular distance from each other (e.g., in the groove 45, e.g., when inflated in the groove 45) defined by an angle of, e.g., less than 180°, less than 90°, less than 45° or less than 10° with respect to axis 35. The aperture 76 may be provided on one of these free ends 77, 78 or an aperture 76 may be provided on each of the free ends 77, 78. When the elongate outer member 75/clamping member 80 only extends partially around circumferential groove 45 and accordingly comprises free ends, it may have a rigidity caused by a substance, e.g., by a curing substance (that may be cured).

Figure 15A:
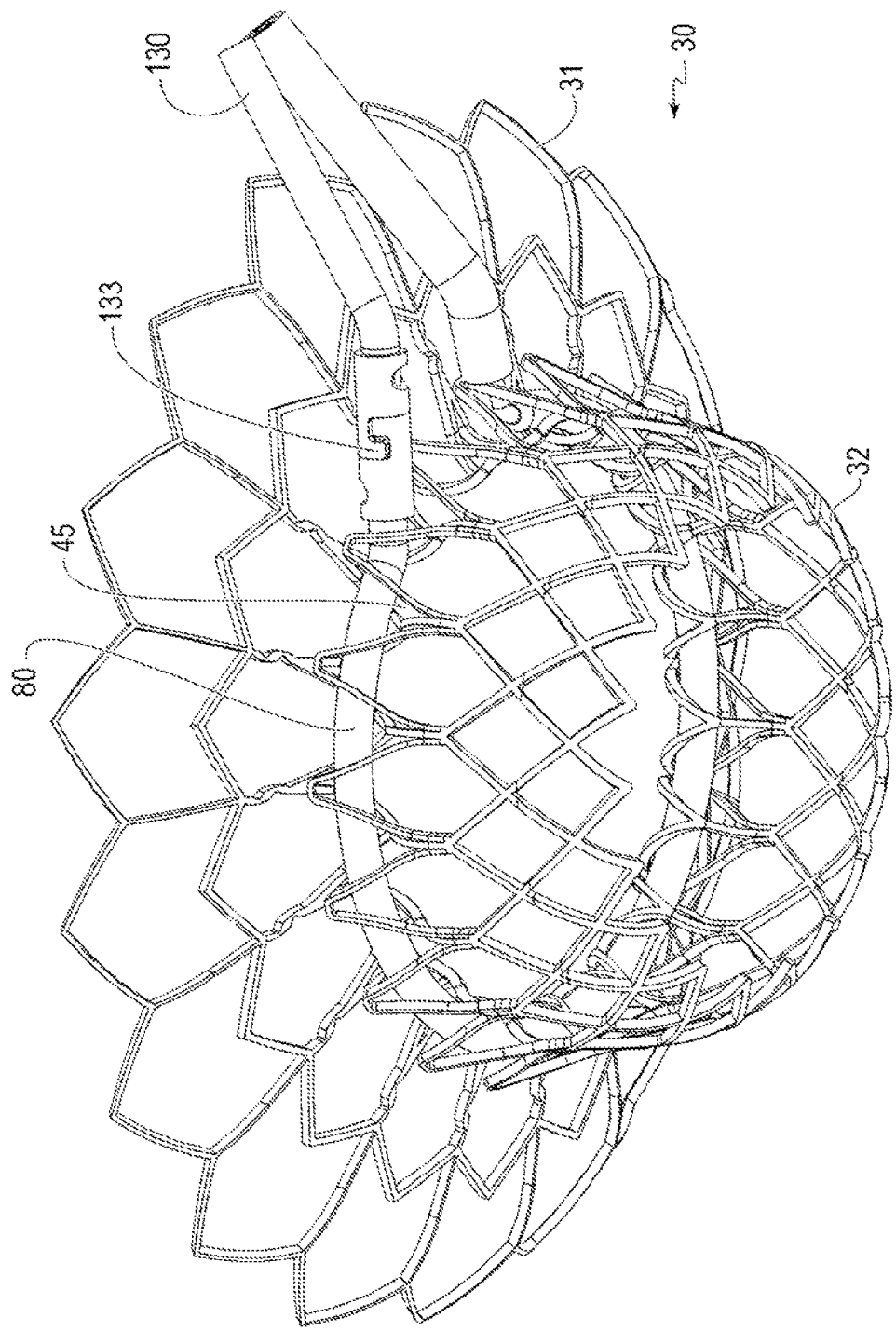
Figure 15B:
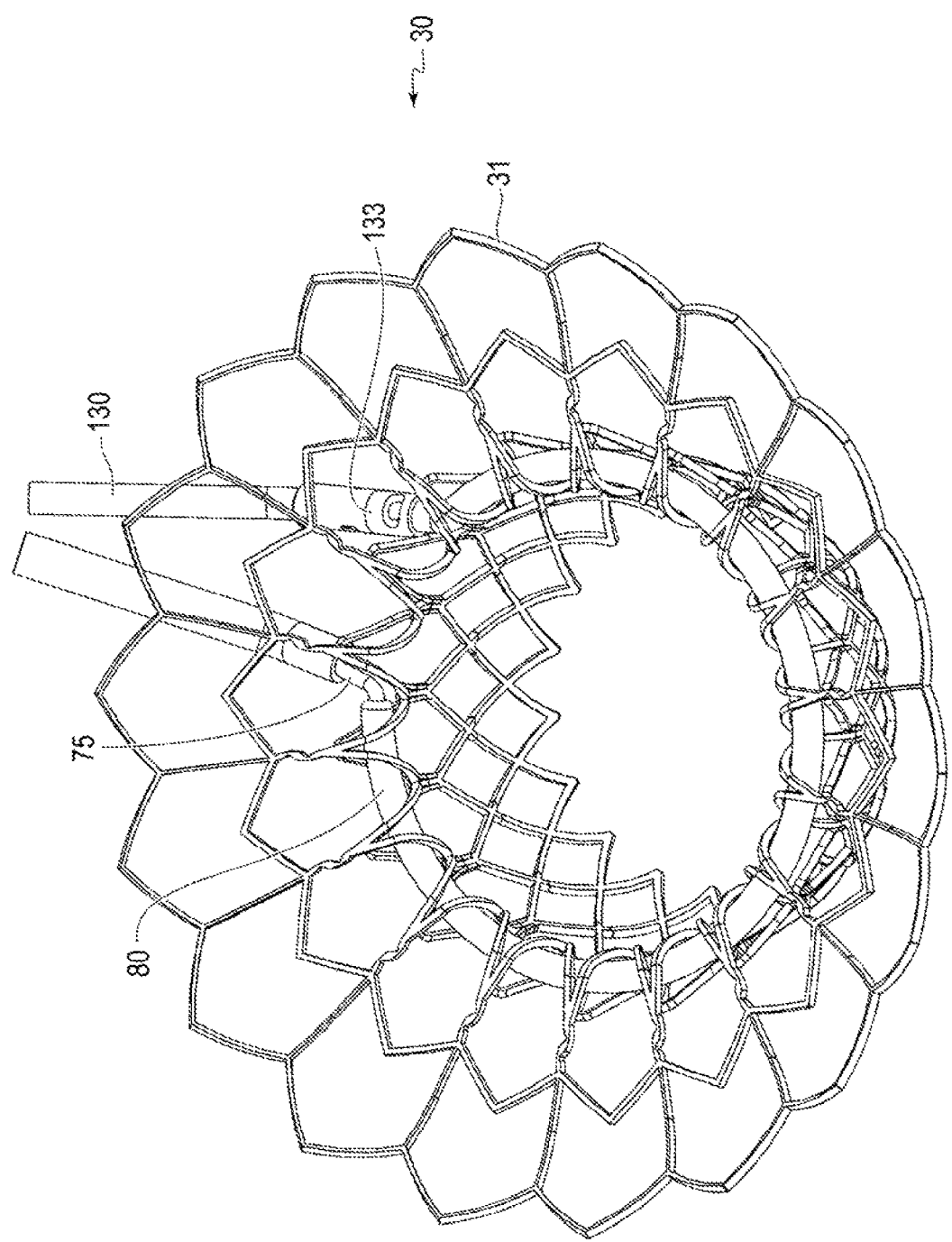
Figure 15C:
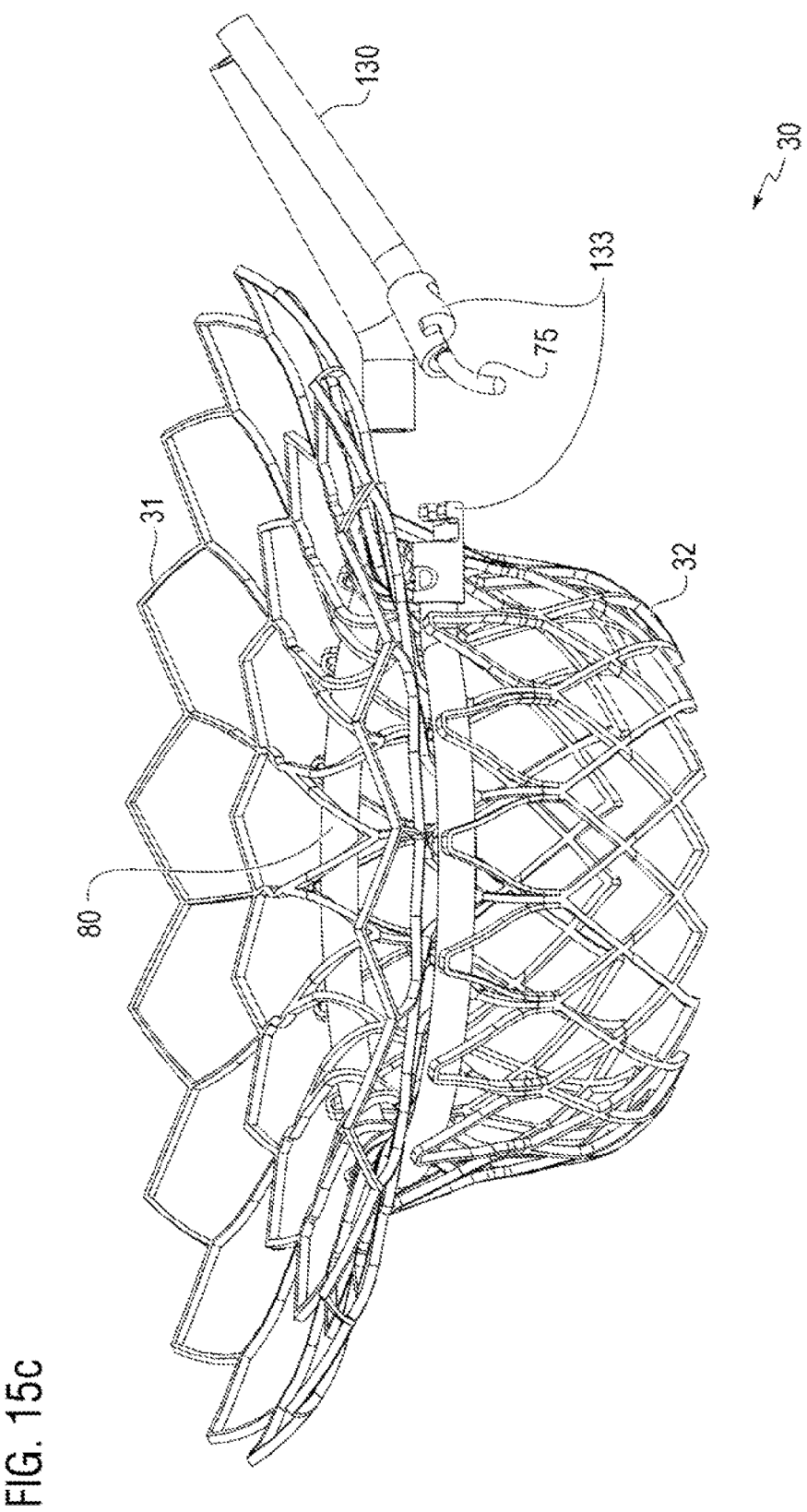

A shown in FIGS. 15a, 15b, and 15c, the clamping member 80 may be guided over the elongate outer member 75 and into the circumferential groove by an insertion member 130. For example, insertion member 130 may be connected to clamping member 80 with a releasable coupling member 133. The insertion member 130 may be configured to push the clamping member 80 into circumferential groove 45 and over elongate outer member 75. In embodiments, the insertion member 130 may be configured to pull the clamping member 80. The coupling member 133 may include an interference fit between the clamping member 80 and the insertion member 130, or for example, the coupling member 133 may include a luer lock, or any suitable releasable latch. The coupling member 133 may be configured to selectively release the clamping member 80 from the insertion member 130 and/or may be configured to selectively re-attach the clamping member 80 to the insertion member 130.

The clamping member 80/elongate outer member 75 (e.g., when it comprises an elastic and/or compressible material, e.g., as described above) may serve to dampen movement of the heart (e.g., caused by the beating heart, e.g., pulse) by acting as a dampening and/or cushioning member between the heart (e.g., a heart chamber) and the prosthesis 1 (e.g., tubular body 30) to further improve the fixation of the prosthesis 1 relative in the heart by reducing forces caused by the beating heart acting on the prosthesis 1 by dampening these forces. Accordingly, the clamping member 80/elongate outer member 75 may absorb movements (e.g., of the ventricular wall (e.g., of the papillary muscle of the ventricular chamber 20) to reduce or avoid pulsation of the prosthesis 1. The clamping member 80 may serve to maintain a distance of the prosthesis 1 from tissue of the heart (e.g., from a wall of the ventricular chamber 20 and/or the atrial chamber 15) and thereby improve placement and/or fixation of the prosthesis 1. Accordingly, the elongate outer member 75 and/or the clamping member 80 may serve as a damping member and/or a spacer member. The clamping member 80 and/or the elongate outer member 75 and hence, the groove 45, may be arranged on a side of the ventricular chamber when seen from the annulus of the natural valve having a distance from the annulus.

The shape of a cross section of tubular body 30 across its longitudinal axis (e.g., axis 35) may vary. Catheter member 90 may comprise or provide a piercing component that can be positioned through the connection channel wall structure 25 (e.g., from an outside of connection channel wall structure 25) and through the tubular body 30 in substantially diametrically opposite positions relatively to an axial (with respect to axis 35) cross section. The piercing component may be hollow and enable placement of an anchor on connection channel wall structure 25 at the distal position of a diameter of the connection channel wall structure 25 relatively to catheter member 90. Said anchor may be attached to a longitudinal end of a longitudinal component (e.g., a tether), which in turn may be provided with a second anchor on its other longitudinal end. The second anchor may be placed by the piercing component upon retrieval of the piercing component from the connection channel wall structure 25 at the proximal end (relative to catheter member 90) of said diameter on connection channel wall structure 25.

The length of said longitudinal component can be designed to be under tension from forces acting on the longitudinal component induced by the first and second anchors, so as to create a deformation of tubular body 30 in a substantially elliptical shape, e.g., the longitudinal component may be shorter than a diameter of the tubular body 30 when no external forces act upon tubular body 30. The longitudinal component may be placed across an inner lumen of tubular body 30 in a position where it does not interfere with the function of valve 40, e.g., be geometrically spaced away from the valve 40. It may be small enough to avoid significant interference with blood flow through tubular body 30, e.g., may have a radius or a diameter ranging from 100 μm to 1000 μm.

In embodiments, the transcatheter valve prosthesis 1 may include fabric 120 disposed at least partially around the tubular body. For example, as shown in FIGS. 16a and 16b, the fabric 120 may be disposed around an outer circumference of tubular body 30 and over second end 69 of projection 55 such that the fabric forms a pouch 22 between the tubular body 30 and projection 55. The pouch 122 serves to prevent tissue and/or the clamping member 80 from sliding down too far between the tubular body and projection 55. For example, the pouch 122 may correspond to chamber 66 disposed between tubular body 30 and projections 50 and/or 55. In embodiments, the tubular body 30 may include the second plurality of projections 55 and the fabric 120 may be disposed over the second end 69 of the second plurality of projections 55 (FIG. 16b). In embodiments, the fabric 120 may be disposed over both the first and second plurality of projections 50, 55.

Figure 17A:
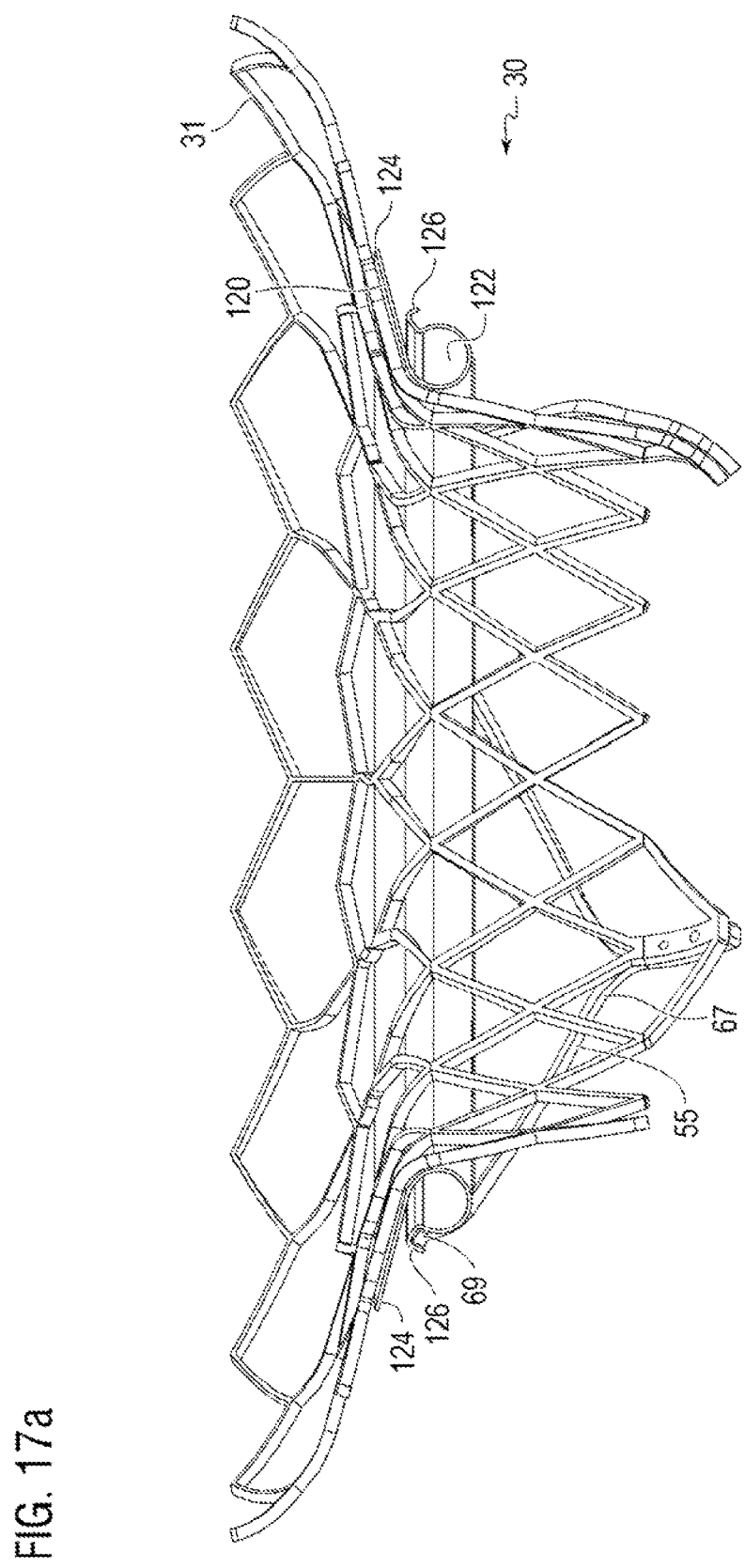
Figure 17B:
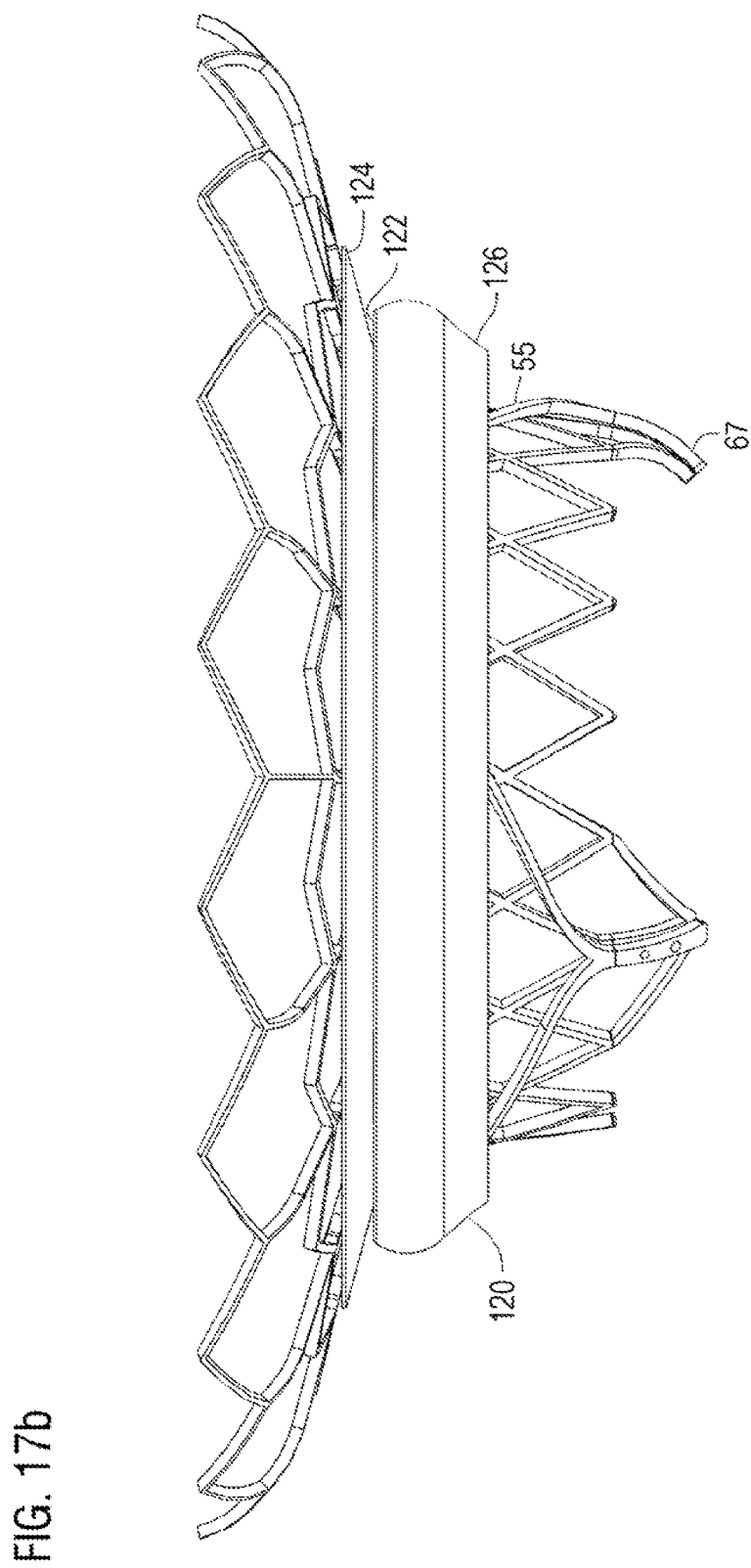
Figure 17C:
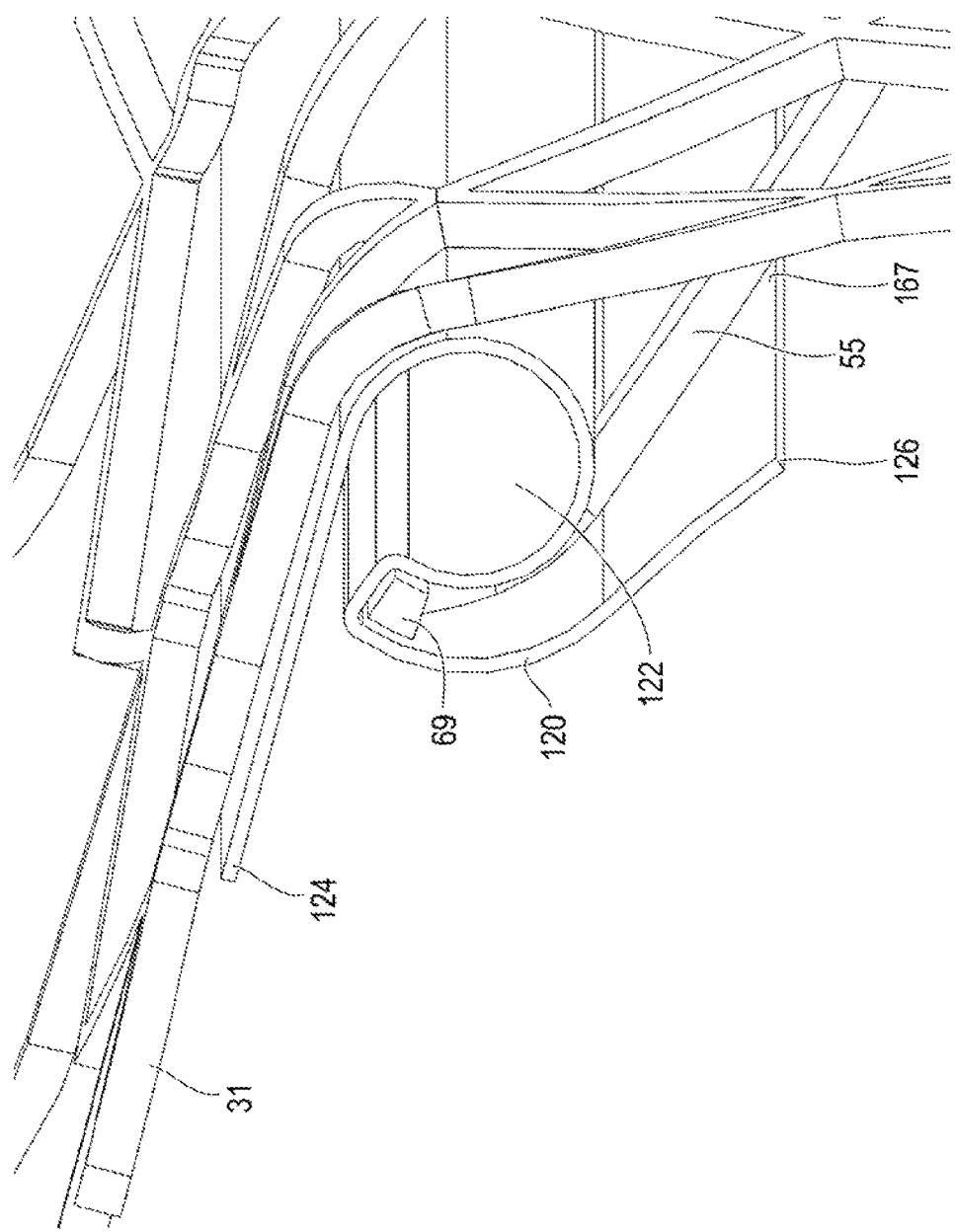
Figure 17D:
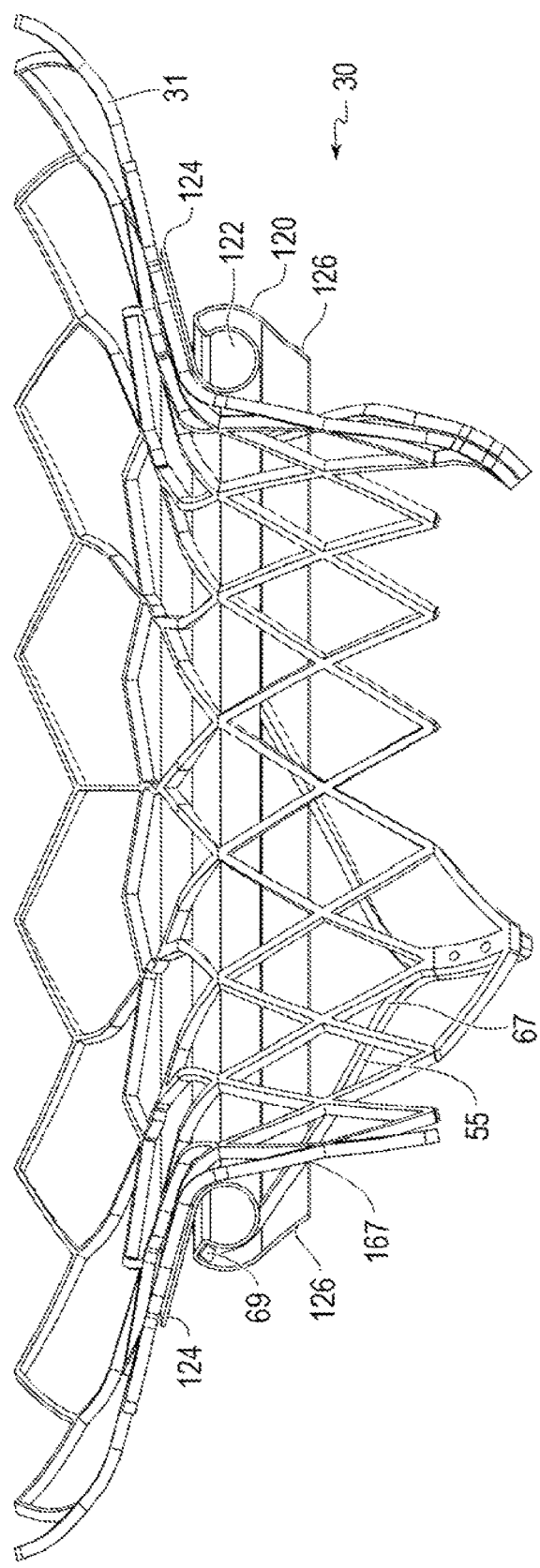

The fabric 120 may comprise liner 33b, as described above, and may include a first end 124 attached to the inflow end of the tubular body 30 and a second end 126 as shown in FIGS. 16a and 16b. The fabric 120 between the first end 124 and the second end 126 may include sufficient slack to form pouch 122. In embodiments, the second end 126 may be attached to the tubular body 30 in a vicinity of the outflow end of the tubular body 30. Alternatively, the second end 126 of the fabric 120 may be attached to the second end 69 of a projection 50, 55, as shown in FIGS. 17a, 17b, 17c, 17d, and 17e. The second end 126 may be attached at a very distal end of second end 69 (FIG. 17a), or the second end 126 may be attached at a connection point 167 that is adjacent to the very distal end of second end 69 (FIGS. 17c and 17d). The fabric 120 may be attached to the tubular body 30 or projection 50, 55 by, for example, sutures, adhesives, clamps, or any attachment means known in the art. In embodiments, the second end 126 may be unattached to the tubular body 30 and include a free end, as shown in FIG. 18. The free end of second end 126 may extend substantially the entire length of stent 30 (FIGS. 16a, 16b, and 18), or the free end of second end 126 may be shorter than the length of the stent, for example as shown in FIGS. 17b-17e. In other embodiments, the length of second end 126 may be shorter or longer than the embodiments shown in FIG. 16a through FIG. 18.

The fabric 120 may include one or more segments of material. In embodiments, the fabric 120 includes one segment of material that completely circumscribes the tubular body 30. In embodiments, the fabric 120 may include multiple segments, for example, two, four, or six. The segments may be spaced apart, providing gaps between adjacent segments. Alternatively or in addition, some or all adjacent segments may overlap. The fabric 120 maybe continuous with, for example, liner 33b (FIG. 6a). The fabric 120 may be made from polyester fabric (e.g., DACRON® or other PTFE graft material).

Figure 17E:
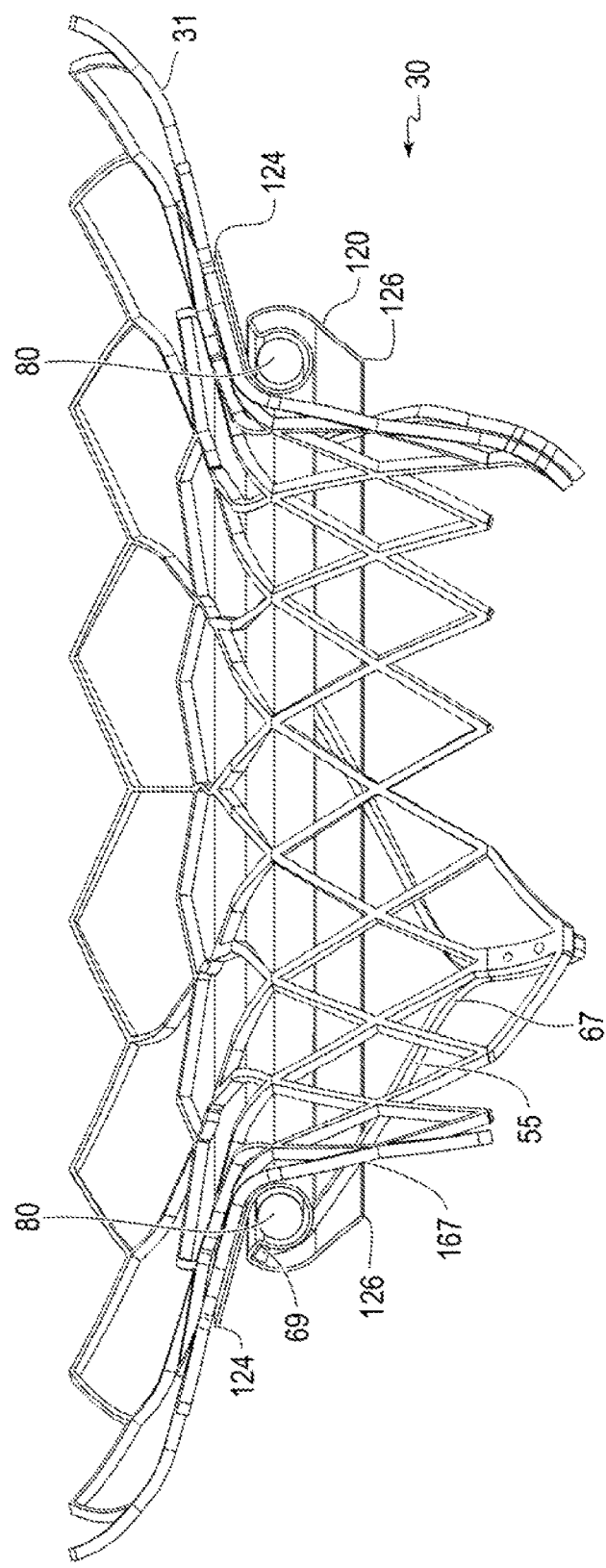
Figure 18:
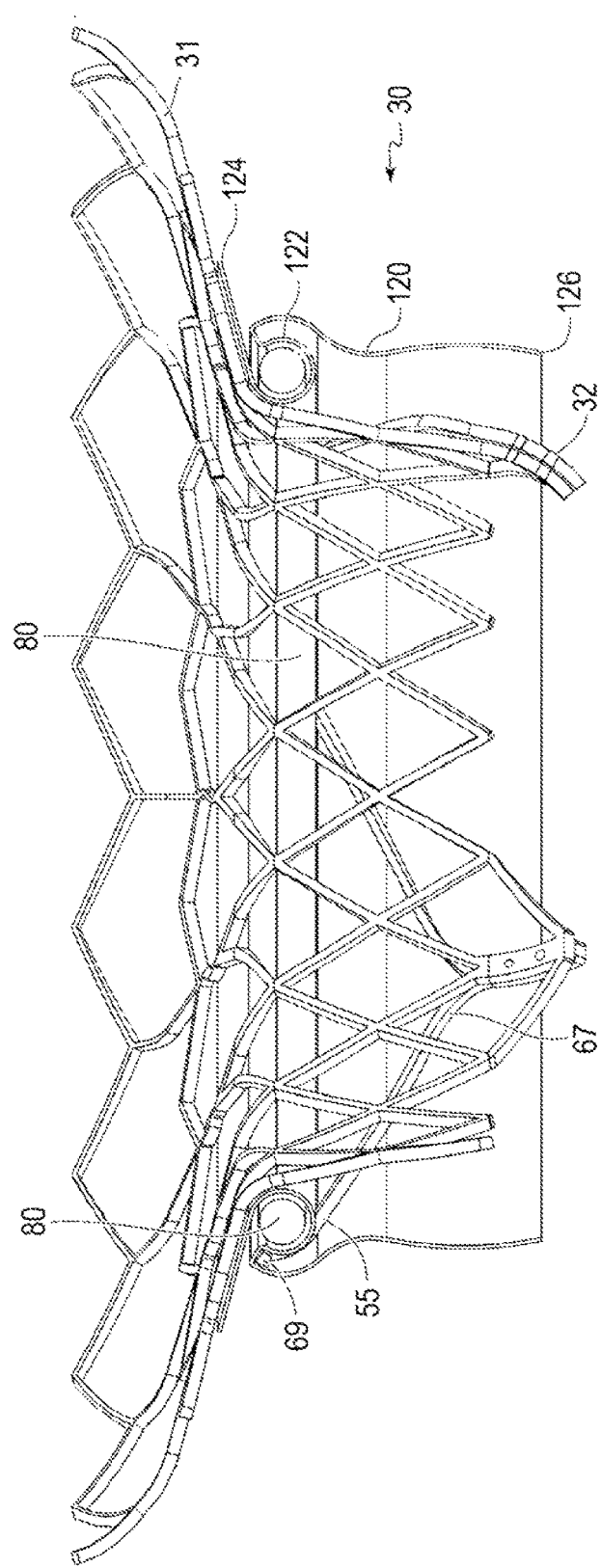

Elongate outer member 75 and clamping member 80 may be moved into the pouch 122 and trap tissue within the pouch 122, for example as shown in FIG. 17e. Movement of the elongate outer member and/or clamping member 80 into the pouch 122 may provide tension on fabric 120, causing the fabric 120 to be taut. Thereby, the tissue may be trapped between the tubular body 30 and the projection 55. The fabric 120 may then located between the tubular body 30 and the trapped portions of tissue (e.g., native valve leaflets and/or chords), and between the trapped portions of tissue and the projection 55.

In embodiments, the fabric 120 may be attached to tubular body 30 with sufficient slack to form a pouch, but the pouch 122 may not be formed until elongate outer member 75 and/or clamping member 80 is/are moved into contact with the fabric 120 between the tubular body 30 and the projection 55. Then the elongate outer member 75 and/or clamping member 80 forms the pouch 122 such that the size of the pouch 122 corresponds to the size of the elongate outer member 75 and/or clamping member 80.

As shown in FIGS. 26 and 27, the barbs 230 may be configured to at least partially pierce through fabric 120 when the barbs 230 pierce the portions of native valve leaflets and/or chords. The piercing of the fabric 120 by barbs 230 may help to secure the prosthesis to the native valve leaflets and/or chords.

All embodiments of the transcatheter valve prosthesis 1 may comprise positioning and/or orientation devices to facilitate relative and/or absolute positioning of the tubular body 30 and/or the elongate outer member 75 and/or the clamping member 80. These devices may include passive markers that are fixedly attached to the tubular body 30 and/or the elongate outer member 75 and/or the clamping member 80. The passive markers may be made from materials different from the materials of the tubular body 30 and/or the elongate outer member 75 and/or the clamping member 80 in order to improve contrast during medical imaging, e.g., using magnetic resonance or X-ray based imaging techniques. The passive markers may, e.g., be made of highly radio-opaque materials thereby allowing one to precisely acquire the relative and/or absolute position of the components of the transcatheter valve prosthesis 1 with respect to the patient's body. The passive markers may each have an asymmetrical shape so as to allow identification of the absolute and/or relative position and orientation and thereby the position and orientation of the tubular body 30 and/or the elongate outer member 75 and/or the clamping member 80. The passive markers may have an identical shape and may be arranged in a certain configuration relative to each other to allow recognition of the orientation. The circumferential groove 45 of the tubular body 30 and/or the tubular body 30 and/or the elongate outer member 75 and/or the clamping member 80 may have passive markers fixedly attached to facilitate positioning them relative to each other using imaging techniques, e.g., passive markers made of highly radio-opaque materials when imaging techniques based on electro-magnetic radiation (e.g., X-ray imaging) are used. In addition and/or as an alternative, the circumferential groove 45 and/or other parts/components of the tubular body 30 and/or the elongate outer member 75 and/or the clamping member 80 may be made from radio-opaque materials.

A method for using a transcatheter prosthesis 1 as described above may comprise:

Placing the transcatheter valve prosthesis 1 within an atrio-ventricular valve, e.g., in a mitral or a tricuspid valve of a human or animal heart, via an insertion catheter. The transcatheter valve prosthesis 1 may, e.g., be placed in a connection channel wall structure 25 between a ventricular chamber 20 and an atrial chamber 15 as shown in FIG. 1.

To place transcatheter valve prosthesis 1 within the heart valve, the following approaches may be applied: 1) an arterial retrograde approach entering the heart cavity over the aorta, 2) through a venous access and through a puncture through the inter atrial septum (trans-septal approach), 3) over a puncture through the apex of the heart (trans-apical approach), 4) over a puncture through the atrial wall from outside the heart, 5) arterial access (e.g., from the femoral artery through a puncture in the groin), or 6) any other approach known to a skilled person. The approach to the valve is facilitated as the tubular body 30 is radially compressible and extendable and may, e.g., be folded and stuffed in a catheter during approach and may be unfolded/extended when within the circumferential connection channel wall structure 25. The transcatheter valve prosthesis 1 may include the clamping member 80 or the clamping member 80 may be inserted separately via one of the mentioned approaches (e.g., using a catheter) so as to be placed in the circumferential groove 45 of the tubular body 30 when the tubular body 30 is located in the connection channel wall structure 25. The clamping member 80 may be compressible and expandable.

Fixing the transcatheter valve prosthesis 1 in the heart relative to the valve.

For functional replacement of a heart valve, the transcatheter valve prosthesis 1 is fixed relative to the connection channel wall structure 25 and sealed against blood flow on the exterior of the transcatheter valve prosthesis 1 in the connection channel wall structure 25. To achieve this, tissue of the connection channel wall structure 25 adjacent to the circumferential groove 45 may be forced or placed inside the circumferential groove 45 to engage radially below the first 50 and second 55 pluralities of projections whereby the tissue is prevented from slipping out of the groove 45 by the first 50 and/or second 55 plurality of projections, wherein the free ends 60, 65 of the first 50 and/or second plurality 55 of projections may penetrate the tissue. The tissue of the connection channel wall structure 25 may be (completely) perforated, or for example partially perforated, by the projections 50, 55 and may thereby be prevented from slipping out of the circumferential groove 45. The clamping member 80 or two or more clamping members 80 may be provided in the circumferential groove 45 to actively press tissue of the connection channel wall structure 25 against the free ends 60, 65 so as to interlock the tissue with the free ends 60, 65. This results in the transcatheter valve prosthesis 1 being held in place more firmly and sealed against blood flow between the exterior of the tubular body 30 and the connection channel wall structure 25.

To place tissue in the circumferential groove 45 of the tubular body 30, a method for using a transcatheter valve prosthesis 1 may comprise using an elongate outer member 75 to radially and inwardly force tissue of die connection channel wall structure 25 into the circumferential groove 45 (which may or may not comprise a clamping member 80). With reference to FIG. 3, the elongate outer member 75 may be disposed at an exterior of the connection channel wall structure 25 at a level of the circumferential groove 45. Then, with further reference to FIG. 6b, a distance R5 between the elongate outer member 75 and the axis 35 of the tubular body is reduced (that means that also a distance between the bottom 46 of the circumferential groove 45 of the tubular body 30 and the elongate outer member 75 is reduced) so as to force tissue of the connection channel wall structure 25 into the circumferential groove 45 to fix the tissue in the circumferential groove 45. In embodiments, the elongate outer member 75 slides along the slope of a partially deployed tubular body 30 to force tissue of the connection wall structure 25 into the circumferential groove 45. The elongate outer member 75 may be handled via a catheter member 90 and an approach as described in relation to the transcatheter valve prosthesis 1 or any other approach may be used in order to bring the elongate outer member 75 into the vicinity of the connection channel wall structure 25.

After the elongate outer member 75 is disposed within the circumferential groove 45 so as to fix tissue with the groove 45 and the tubular body 30 is fully deployed, the clamping member 80 may be guided along the elongate outer member 75 such that the clamping member 80 is disposed over and coaxial with the loop of the elongate outer member 75 within groove 45. For example, the clamping member 80 may be advanced between at least two stent struts 107 and/or projections on the tubular body 30 in order to be slid over the elongate outer member 75. The clamping member 80 may then trap the tissue (e.g., native valve leaflets and/or chords) within the circumferential groove 45. In embodiments, an insertion member 130 may push the clamping member 80 between the stent struts 107 and over the elongate outer member 75. A coupling member 133 may release the insertion member 130 from the clamping member 80.

In embodiments, the clamping member 80 may be moved into the circumferential groove 45 when the tubular body 30 is partially deployed. For example, when the outflow end but not the inflow end of the tubular body 30 is deployed from a delivery catheter such that the circumferential opening of groove 45 is relatively larger (as compared to when the tubular body 30 is fully deployed), the clamping member 80 may be moved into the circumferential groove 45. The clamping member 80 may be slid along the tubular body 30 (for example, in a direction from the outflow end toward the inflow end of the tubular body 30) into the circumferential groove 45 to trap tissue within the groove.

When the tissue of the connection channel wall structure 25 is held in the circumferential groove 45 by the projections 50, 55, the elongated member 75 (and the catheter member 90) may be removed from the heart or, as shown illustratively in FIG. 7, the connecting means 91 of the catheter member 90 may be used in order to permanently connect two (free) ends of the elongate outer member 75 together and optionally cut the ends so that elongate outer member 75 remains permanently on the exterior of a connection channel wall structure 25 on a level of the circumferential groove 45 of the tubular body 30 so as to additionally hold tissue of the connection channel wall structure 25 in the circumferential groove 45.

In embodiments, elongate outer member 75 may radially and inwardly force tissue of connection channel wall structure 25 into contact with fabric 120 and between the tubular body 30 and the projection 55. This movement of elongate outer member 75 may guide native valve leaflets and/or chords into circumferential groove 45, wherein the circumferential groove 45 is formed between the tubular body 30 and the projection 55. Movement of elongate outer member 75 into circumferential groove 45 may guide the native valve leaflets and/or chords into contact with fabric 120 to form pouch 122. The fabric 120 may thus change from slack to taut to form pouch 122. The clamping member 80 may further be advanced into pouch 122 to trap the tissue within pouch 122.

In embodiments, the insertion member 130 may push the clamping member 80 into the circumferential groove 45 and over the elongate outer member 75. For example, the insertion member 130 may push the clamping member 80 between at least two stent struts 107 and into the circumferential groove 45. The coupling member 133 may selectively release the clamping member 80 from the insertion tube 130 after the clamping member 80 is within the circumferential groove 45 (FIG. 15c). In embodiments, releasing and removing the elongate outer member 75 from the tubular body 30 releases the clamping member 80 from the insertion member 130. The clamping member 80 and the insertion member 130 may be re-attached with the coupling member 130 after the step of releasing the clamping member 80 from the insertion member 130. The clamping member 80 may then be repositioned within the patient. Additionally, the tubular body 30 and elongate outer member 75 may also be repositioned within the patient. After re-positioning the clamping member 80 within the patient, the coupling member 133 may re-release the clamping member 80 from the insertion member 130.

A method for using the transcatheter atrio-ventricular prosthesis 1 may result in the transcatheter valve prosthesis 1 being fixed to the connection channel wall structure 25 and being firmly held in place via the tissue that is held in the circumferential groove 45 by the free ends 60, 65, optionally supported by the clamping member 80 and/or the permanently disposed elongate outer member 75.

A method for using the transcatheter atrio-ventricular prosthesis 1 may also result in fixation of tubular body 30 to the connection channel wall structure 25 with minimal occlusion of the patient's valve. For example, the elongate outer member 75 may be advanced to the patient's native valve within a first delivery catheter, for example through the patient's femoral artery. The elongate outer member 75 may form a loop around the patient's native valve without substantially occluding the valve. The tubular body 30 may be advanced to the patient's native valve within a second delivery catheter, for example through the patient's atrial wall. The tubular body 30 may be partially deployed from the second delivery catheter such that the outflow end but not the inflow end of the tubular body 30 is deployed from the second delivery catheter. Only for the brief time that the tubular body 30 is partially deployed, the patient's native valve may be substantially occluded. The elongate outer member 75 may then move into the circumferential groove 45 when the tubular body is partially deployed, and thereby move the patient's native valve leaflets and/or chords into the groove 45. Once the tubular body 30 is fully deployed, the patient's native valve may no longer be substantially occluded. Therefore, the method may include only substantially occluding the native valve only when the tubular body 30 is partially deployed and not yet anchored in position by elongate outer member 75. Additionally, clamping member 80 may be advanced over the elongate outer member 75 without substantially occluding the native valve. For example, as discussed above, the clamping member may be advanced over the elongate member 75 and around the fully deployed or partially deployed tubular body 30.

Features of the transcather atrio-ventricular valve prosthesis 1 and method steps involving the prosthesis that have been described herein (description and/or figures and/or claims) referring to a transcather atrio-ventricular valve prosthesis 1 comprising first 50 and second 55 pluralities of projections also apply to a transcatheter atrio-ventricular valve prosthesis 1 comprising one plurality of projections (50, 55) and vice versa. In particular, features described in the application (description, claims, figures) to further define the projections of the first and second plurality of projections are also applicable to only the first plurality of projections if, for example, the valve prosthesis only comprises the first plurality of projections. All features herein are disclosed to be interchangeable between all embodiments of the transcather atrio-ventricular valve prosthesis 1.

What is claimed is:

1. A system for implanting a heart valve, comprising:
a radially self-expandable tubular body having an inflow end at a proximal end and an outflow end at a distal end, and a projection extending from a side surface of the tubular body toward the inflow end such that a channel is formed by the tubular body and the projection, the tubular body being configured to move between a compressed, delivery state and an expanded, deployed state; and
a fabric attached to the tubular body and covering at least a terminal, free end of the projection such that the fabric forms a pouch in the channel, the pouch being configured to prevent tissue and/or a trapping member from sliding down too far between the tubular body and the projection;
wherein
the channel has a distal-most point at a position where a radially inward surface of the projection attaches to the side surface of the tubular body, the fabric has a first end attached to an inflow side of the tubular body, and the fabric extends distally from the first end over the tubular body, and covers the terminal, free end of the projection such that a distal-most point of the pouch is suspended between the tubular body and the projection and is proximally spaced from the distal-most point of the channel ; and
the tubular body is configured to have a valve disposed therein and attached thereto.

2. The system according to claim 1, further including an elongate outer member configured to be moved into the pouch and guide heart tissue into the pouch such that the heart tissue is between the tubular body and the elongate outer member.

3. The system according to claim 2, further including a trapping member configured to be disposed along the elongate outer member and trap the heart tissue in the pouch.

4. The system according to claim 3, wherein the fabric is configured to move from a slack state to a tensioned state when the trapping member moves between the projection and the tubular body.

5. The system according to claim 1, wherein the fabric further includes a second end attached to the tubular body in the vicinity of the outflow end.

6. The system according to claim 1, wherein the fabric further includes a second end attached to the projection.

7. The system according to claim 1, wherein the fabric is polyester fabric.

8. The system according to claim 1, wherein the fabric further includes a second end that is radially spaced from the out flow end of the tubular body.

9. The system according to claim 1, wherein the fabric further includes a second end such that the outflow end of the tubular body curves radially inward and the second end of the fabric is configured to curve radially outward.

10. The system according to claim 1, wherein
the first end of the fabric is distal of a proximal-most end of the tubular body in an outflow direction.

11. The system according to claim 1, wherein the distal-most point of the pouch is not fixed to the tubular body or the projection.

12. A system for implanting a heart valve, comprising:
a radially self-expandable tubular body having an inflow end at a proximal end and an outflow end at a distal end, and a projection extending from a side surface of the tubular body toward the inflow end such that a channel is formed by the tubular body and the projection, the tubular body being configured to move between a compressed, delivery state and an expanded, deployed state;
a fabric attached to the tubular body; and
an elongate outer member configured to be moved into contact with the fabric such that the fabric forms a pouch in the channel, the pouch being configured to prevent tissue and/or a trapping member from sliding down too far between the tubular body and the projection;
wherein:
the channel has a distal-most point at a position where a radially inward surface of the projection attaches to the side surface of the tubular body, the fabric has a first end attached to an inflow side of the tubular body, and the fabric extends distally from the first end over the tubular body, and covers the terminal, free end of the projection such that a distal-most point of the pouch is suspended between the tubular body and the projection, and is proximally spaced from the distal-most point of the channel; and
the tubular body is configured to have a valve disposed therein and attached thereto.

13. The system according to claim 12, wherein the elongate outer member is configured to guide heart tissue into the pouch such that the heart tissue is between the tubular body and the elongate outer member.

14. The system according to claim 12, wherein the fabric is configured to move from a slack state to a tensioned state when the elongate outer member moves into contact with the fabric between the projection and the tubular body.

15. The system according to claim 12, wherein the distal-most point of the pouch is not attached to the tubular body or the projection.

* * * * *